United States Patent
Bonutti et al.

(10) Patent No.: US 9,980,871 B2
(45) Date of Patent: *May 29, 2018

(54) KNEE ORTHOSIS

(71) Applicant: BONUTTI RESEARCH, INC., Effingham, IL (US)

(72) Inventors: Boris P. Bonutti, Effingham, IL (US); Peter M. Bonutti, Manalapan, FL (US); Glen A. Phillips, Effingham, IL (US)

(73) Assignee: Bonutti Research, Inc., Effingham, IL (US)

( * ) Notice: Subject to any disclaimer, the term of this patent is extended or adjusted under 35 U.S.C. 154(b) by 71 days.

This patent is subject to a terminal disclaimer.

(21) Appl. No.: 14/584,759

(22) Filed: Dec. 29, 2014

(65) Prior Publication Data

US 2015/0119764 A1    Apr. 30, 2015

Related U.S. Application Data

(63) Continuation of application No. 12/026,112, filed on Feb. 5, 2008, now Pat. No. 8,920,346.

(Continued)

(51) Int. Cl.
*A61H 1/02* (2006.01)
*A61F 5/01* (2006.01)
*A61H 1/00* (2006.01)

(52) U.S. Cl.
CPC .......... *A61H 1/024* (2013.01); *A61F 5/0125* (2013.01); *A61H 1/00* (2013.01); *A61H 1/02* (2013.01);

(Continued)

(58) Field of Classification Search
CPC .......... A61H 1/00; A61H 1/02; A61H 1/0237; A61H 1/024; A61H 1/0244; A61H 1/0255;

(Continued)

(56) References Cited

U.S. PATENT DOCUMENTS 432,327 A   7/1890   Page
433,227 A   7/1890   Beacock
(Continued)

FOREIGN PATENT DOCUMENTS

CA   2065669   4/1995
CA   2066151   5/1997
(Continued)

OTHER PUBLICATIONS

Smith & Nephew DonJoy Inc., Quadrant Shoulder Brace, http://www.shoulder.com/quadrant.html, Jun. 5, 1998, 1 page.

(Continued)

*Primary Examiner* — Colin W Stuart
(74) *Attorney, Agent, or Firm* — Senniger Powers LLP

(57) ABSTRACT

An orthosis for stretching tissue around a joint of a patient between first and second relatively pivotable body portions. The orthosis includes a first arm member affixable to the first body portion and including a first extension member extending therefrom. A second arm member affixable to the second body portion is also included and has a second extension member having an arcuate shape extending therefrom. A third arm member including a third extension member having an arcuate shape extending therefrom is interposed between the first and second arm members. The third extension member is slidably connected to the first arm member and the second extension member is operatively connected to the third arm members, such that the second arm members travel along an arcuate path defined by the second extension member when the second arm member is moved from a first position to a second position relative to the first and third arm members. Furthermore, the position of the third arm member can be securely adjusted relative the first arm member.

5 Claims, 28 Drawing Sheets

Related U.S. Application Data

(60) Provisional application No. 60/888,107, filed on Feb. 5, 2007.

(52) U.S. Cl.
CPC .... *A61H 1/0237* (2013.01); *A61F 2005/0139* (2013.01); *A61F 2005/0153* (2013.01); *A61H 1/0244* (2013.01); *A61H 1/0266* (2013.01); *A61H 1/0274* (2013.01); *A61H 1/0277* (2013.01); *A61H 1/0281* (2013.01); *A61H 1/0285* (2013.01); *A61H 1/0288* (2013.01)

(58) Field of Classification Search
CPC .. A61H 1/0266; A61H 1/0274; A61H 1/0277; A61H 1/0281; A61H 1/0285; A61H 1/0288; A61H 2001/0203; A61H 2001/0207; A61H 2001/0211
USPC ..... 601/5, 23, 27, 33, 34, 35, 84, 97; 602/5, 602/23, 26, 27
See application file for complete search history.

(56) References Cited

U.S. PATENT DOCUMENTS

| | | |
|---|---|---|
| 2,191,283 A | 2/1940 | Longfellow |
| 2,206,902 A | 7/1940 | Kost |
| 2,223,276 A | 11/1940 | Ward |
| 2,237,252 A | 4/1941 | Longfellow |
| 2,246,689 A | 6/1941 | Kost |
| 2,250,493 A | 7/1941 | Milne |
| 2,590,729 A | 3/1952 | Scognamillo |
| 2,590,739 A | 3/1952 | Wagner et al. |
| 2,811,154 A | 10/1957 | Scholl |
| 2,820,455 A | 1/1958 | Hall |
| 2,829,562 A | 4/1958 | La Rue |
| 2,832,334 A | 4/1958 | Whitelaw |
| 3,083,708 A | 4/1963 | Gottfried |
| 3,338,237 A | 8/1967 | Sconce |
| 3,351,055 A | 11/1967 | Gottfried |
| 3,548,818 A | 12/1970 | Kaplan |
| 3,580,248 A | 5/1971 | Larson |
| 3,698,389 A | 10/1972 | Guedel |
| 3,701,349 A | 10/1972 | Larson |
| 3,724,452 A | 4/1973 | Nitschke |
| 3,760,056 A | 9/1973 | Rudy |
| 3,795,243 A | 3/1974 | Miller |
| 3,811,434 A | 5/1974 | Jacobson et al. |
| 3,814,419 A | 6/1974 | Bjorklund et al. |
| 3,856,004 A | 12/1974 | Cox |
| 3,955,565 A | 5/1976 | Johnson, Jr. |
| 3,970,316 A | 7/1976 | Westmoreland, Jr. |
| 3,976,057 A | 8/1976 | Barclay |
| 4,039,183 A | 8/1977 | Sakurada |
| 4,076,022 A | 2/1978 | Walker |
| 4,084,267 A | 4/1978 | Zadina |
| 4,108,170 A | 8/1978 | Spann |
| 4,180,870 A | 1/1980 | Radulovic et al. |
| 4,214,577 A | 7/1980 | Hoy |
| 4,229,001 A | 10/1980 | Roman |
| 4,237,873 A | 12/1980 | Terry et al. |
| 4,241,731 A | 12/1980 | Pauley |
| 4,273,113 A | 6/1981 | Hofstein |
| 4,285,773 A | 8/1981 | Taciuk |
| 4,320,748 A | 3/1982 | Racette et al. |
| 4,363,481 A | 12/1982 | Erickson |
| 4,370,977 A | 2/1983 | Mauldin et al. |
| 4,383,523 A | 5/1983 | Schurman |
| 4,417,569 A | 11/1983 | Brudny |
| 4,441,489 A | 4/1984 | Evans et al. |
| 4,454,871 A | 6/1984 | Mann et al. |
| 4,456,001 A | 6/1984 | Pescatore |
| 4,456,002 A | 6/1984 | Barber et al. |
| 4,502,470 A | 3/1985 | Kiser et al. |
| 4,502,681 A | 3/1985 | Blomqvist |
| 4,508,111 A | 4/1985 | Hepburn |
| 4,509,509 A | 4/1985 | Bouvet et al. |
| 4,538,595 A | 9/1985 | Hajianpour |
| 4,538,600 A | 9/1985 | Hepburn |
| 4,570,619 A | 2/1986 | Gamm |
| 4,576,151 A | 3/1986 | Carmichael et al. |
| 4,589,406 A | 5/1986 | Florek |
| 4,606,542 A | 8/1986 | Segal |
| 4,612,919 A | 9/1986 | Best |
| 4,628,913 A | 12/1986 | Lerman |
| 4,641,639 A | 2/1987 | Padilla |
| 4,653,479 A | 3/1987 | Maurer |
| 4,665,905 A | 5/1987 | Brown |
| 4,688,559 A | 8/1987 | Vito et al. |
| 4,693,239 A | 9/1987 | Clover, Jr. |
| 4,716,889 A | 1/1988 | Saringer |
| 4,718,665 A | 1/1988 | Airy et al. |
| 4,727,865 A | 3/1988 | Hill-Byrne |
| 4,739,334 A | 4/1988 | Soref |
| 4,765,320 A | 8/1988 | Lindemann et al. |
| 4,788,941 A | 12/1988 | Villeneuve |
| 4,790,301 A | 12/1988 | Silfverskiold |
| 4,793,334 A | 12/1988 | McGuinness et al. |
| 4,805,601 A | 2/1989 | Eischen, Sr. |
| 4,807,601 A | 2/1989 | Wright |
| 4,809,688 A | 3/1989 | Aymerica del Valle et al. |
| 4,834,073 A | 5/1989 | Bledsoe et al. |
| 4,844,094 A | 7/1989 | Grim |
| 4,844,454 A | 7/1989 | Rogers |
| 4,844,455 A | 7/1989 | Funkhouser, Jr. |
| 4,848,326 A | 7/1989 | Lonardo |
| 4,862,877 A | 9/1989 | Barber |
| 4,865,024 A | 9/1989 | Hensley et al. |
| 4,869,267 A | 9/1989 | Grim et al. |
| 4,869,499 A | 9/1989 | Schiraldo |
| 4,884,454 A | 12/1989 | Johnson |
| 4,913,135 A | 4/1990 | Mattingly |
| 4,913,755 A | 4/1990 | Grim |
| 4,930,497 A | 6/1990 | Saringer |
| 4,953,543 A | 9/1990 | Grim et al. |
| 4,955,369 A | 9/1990 | Bledsoe et al. |
| 4,955,396 A | 9/1990 | Fralick et al. |
| 4,957,281 A | 9/1990 | Christolear, Jr. |
| 4,964,402 A | 10/1990 | Grim et al. |
| 4,991,234 A | 2/1991 | Greenburg |
| 4,996,979 A | 3/1991 | Grim et al. |
| 5,005,563 A | 4/1991 | Veale |
| 5,018,514 A | 5/1991 | Grood et al. |
| 5,019,050 A | 5/1991 | Lynn et al. |
| 5,025,782 A | 6/1991 | Salerno |
| 5,027,688 A | 7/1991 | Suzuki et al. |
| 5,027,801 A | 7/1991 | Grim |
| 5,027,802 A | 7/1991 | Donohue |
| 5,036,837 A | 8/1991 | Mitchell et al. |
| 5,036,838 A | 8/1991 | Sherman |
| 5,052,375 A | 10/1991 | Stark et al. |
| 5,052,379 A | 10/1991 | Airy et al. |
| 5,060,640 A | 10/1991 | Rasmusson |
| 5,070,866 A | 12/1991 | Alexander et al. |
| 5,078,128 A | 1/1992 | Grim et al. |
| 5,088,481 A | 2/1992 | Darby |
| 5,100,403 A | 3/1992 | Hotchkiss et al. |
| 5,102,411 A | 4/1992 | Hotchkiss et al. |
| 5,116,359 A | 5/1992 | Moore |
| 5,125,400 A | 6/1992 | Johnson, Jr. |
| 5,135,470 A | 8/1992 | Reeves |
| 5,139,475 A | 8/1992 | Robicsek |
| 5,141,489 A | 8/1992 | Sereboff |
| 5,156,589 A | 10/1992 | Langen et al. |
| 5,163,451 A | 11/1992 | Grellas |
| 5,167,612 A | 12/1992 | Bonutti |
| 5,191,903 A | 3/1993 | Donohue |
| 5,197,942 A | 3/1993 | Brady |
| 5,201,702 A | 4/1993 | Mars |
| 5,201,772 A | 4/1993 | Maxwell |
| 5,201,776 A | 4/1993 | Freeman |
| 5,203,321 A | 4/1993 | Donovan et al. |
| 5,211,161 A | 5/1993 | Stef |
| 5,213,094 A | 5/1993 | Bonutti |

(56) References Cited

U.S. PATENT DOCUMENTS

| | | |
|---|---|---|
| 5,213,095 A | 5/1993 | Dague |
| 5,218,954 A | 6/1993 | van Bemmelen |
| 5,226,245 A | 7/1993 | Lamont |
| 5,232,435 A | 8/1993 | Leibinsohn |
| 5,252,101 A | 10/1993 | Rosenwinkel et al. |
| 5,252,102 A | 10/1993 | Singer et al. |
| 5,261,125 A | 11/1993 | Cartwright et al. |
| 5,277,695 A | 1/1994 | Johnson, Jr. et al. |
| 5,285,773 A | 2/1994 | Bonutti et al. |
| 5,297,540 A | 3/1994 | Kaiser et al. |
| 5,312,322 A | 5/1994 | Santana |
| 5,316,022 A | 5/1994 | Schiek, Sr. |
| 5,323,435 A | 6/1994 | Baversten |
| RE34,661 E | 7/1994 | Grim |
| 5,327,882 A | 7/1994 | Saringer et al. |
| 5,328,448 A | 7/1994 | Gray, Sr. |
| 5,329,705 A | 7/1994 | Grim et al. |
| 5,348,530 A | 9/1994 | Grim et al. |
| 5,349,956 A | 9/1994 | Bonutti |
| 5,352,216 A | 10/1994 | Shiono et al. |
| 5,354,260 A | 10/1994 | Cook |
| 5,364,323 A | 11/1994 | Liu |
| 5,365,947 A | 11/1994 | Bonutti |
| 5,370,133 A | 12/1994 | Darby et al. |
| 5,372,597 A | 12/1994 | Hotchkiss et al. |
| 5,376,091 A | 12/1994 | Hotchkiss et al. |
| 5,378,223 A | 1/1995 | Grim et al. |
| 5,385,536 A | 1/1995 | Burkhead et al. |
| 5,389,065 A | 2/1995 | Johnson, Jr. |
| 5,391,132 A | 2/1995 | Greenwald |
| 5,395,303 A | 3/1995 | Bonutti et al. |
| 5,399,152 A | 3/1995 | Habermeyer et al. |
| 5,403,265 A | 4/1995 | Berguer et al. |
| 5,407,420 A | 4/1995 | Bastyr et al. |
| 5,407,422 A | 4/1995 | Matthijs et al. |
| 5,417,643 A | 5/1995 | Taylor |
| 5,419,757 A | 5/1995 | Daneshvar |
| 5,421,874 A | 6/1995 | Pearce |
| 5,435,009 A | 7/1995 | Schild et al. |
| 5,437,611 A | 8/1995 | Stern |
| 5,437,619 A | 8/1995 | Malewicz et al. |
| 5,452,205 A | 9/1995 | Telepko |
| 5,453,075 A | 9/1995 | Bonutti et al. |
| 5,453,082 A | 9/1995 | Lamont |
| 5,456,268 A | 10/1995 | Bonutti |
| 5,456,286 A | 10/1995 | Warner et al. |
| 5,464,385 A | 11/1995 | Grim |
| 5,466,213 A | 11/1995 | Hogan et al. |
| 5,466,250 A | 11/1995 | Johnson, Jr. et al. |
| 5,472,407 A | 12/1995 | Schenck |
| 5,472,410 A | 12/1995 | Hamersly |
| 5,492,133 A | 2/1996 | McVicker |
| 5,503,619 A | 4/1996 | Bonutti |
| 5,503,622 A | 4/1996 | Wehr |
| 5,503,908 A | 4/1996 | Faass |
| 5,518,009 A | 5/1996 | Ruiz-Gonzalez |
| 5,520,181 A | 5/1996 | Kreidler et al. |
| 5,520,620 A | 5/1996 | Johnson |
| 5,520,628 A | 5/1996 | Wehr |
| 5,527,269 A | 6/1996 | Reithofer |
| 5,531,669 A | 7/1996 | Varnau |
| 5,535,274 A | 7/1996 | Braitberg et al. |
| 5,538,486 A | 7/1996 | France et al. |
| 5,571,077 A | 11/1996 | Klearman et al. |
| 5,575,764 A | 11/1996 | Van Dyne |
| 5,577,998 A | 11/1996 | Johnson, Jr. et al. |
| 5,605,535 A | 2/1997 | Lepage |
| 5,609,570 A | 3/1997 | Lamont |
| 5,611,764 A | 3/1997 | Bonutti et al. |
| 5,620,411 A | 4/1997 | Schumann et al. |
| 5,626,537 A | 5/1997 | Danyo et al. |
| 5,647,378 A | 7/1997 | Farnum |
| 5,653,680 A | 8/1997 | Cruz |
| 5,665,059 A | 9/1997 | Klearman et al. |
| 5,681,269 A | 10/1997 | Basaj et al. |
| 5,685,830 A | 11/1997 | Bonutti |
| 5,749,840 A | 5/1998 | Mitchell et al. |
| 5,755,679 A | 5/1998 | Seiner et al. |
| 5,761,834 A | 6/1998 | Grim et al. |
| 5,772,619 A | 6/1998 | Corbett |
| 5,778,565 A | 7/1998 | Holt et al. |
| 5,788,659 A | 8/1998 | Haas |
| 5,792,084 A | 8/1998 | Wilson et al. |
| 5,820,577 A | 10/1998 | Taylor |
| 5,823,975 A | 10/1998 | Stark et al. |
| 5,833,639 A | 11/1998 | Nunes et al. |
| 5,839,139 A | 11/1998 | Fink |
| 5,848,979 A | 12/1998 | Bonutti et al. |
| 5,865,773 A | 2/1999 | Koledin |
| 5,882,320 A | 3/1999 | Peterson |
| 5,882,323 A | 3/1999 | Belkin |
| 5,919,148 A | 7/1999 | Marko et al. |
| 5,929,782 A | 7/1999 | Stark et al. |
| 5,940,992 A | 8/1999 | Darby |
| 5,943,705 A | 8/1999 | Sink |
| 5,951,499 A | 9/1999 | Saringer et al. |
| 5,980,435 A | 11/1999 | Joutras et al. |
| 6,001,075 A | 12/1999 | Clemens et al. |
| 6,007,500 A | 12/1999 | Quintinskie, Jr. |
| 6,021,780 A | 2/2000 | Darby |
| 6,027,468 A | 2/2000 | Pick |
| 6,053,169 A | 4/2000 | Hunt |
| 6,059,576 A | 5/2000 | Brann |
| 6,093,162 A | 7/2000 | Fairleigh et al. |
| 6,099,489 A | 8/2000 | Herzberg et al. |
| 6,113,562 A | 9/2000 | Bonutti et al. |
| 6,142,964 A | 11/2000 | Gilmour |
| 6,142,965 A | 11/2000 | Mathewson |
| 6,155,994 A | 12/2000 | Hubbard et al. |
| 6,179,747 B1 | 1/2001 | Kelley |
| 6,179,800 B1 | 1/2001 | Torrens |
| 6,184,797 B1 | 2/2001 | Stark et al. |
| 6,228,044 B1 | 5/2001 | Jensen et al. |
| 6,267,742 B1 | 7/2001 | Krivosha et al. |
| 6,296,595 B1 | 10/2001 | Stark et al. |
| 6,371,123 B1 | 4/2002 | Stark et al. |
| 6,384,755 B1 | 5/2002 | Hayden |
| 6,409,691 B1 | 6/2002 | Dakin et al. |
| 6,436,058 B1 | 8/2002 | Krahner et al. |
| 6,485,447 B1 | 11/2002 | Lavery et al. |
| 6,502,577 B1 | 1/2003 | Bonutti |
| 6,503,213 B2 | 1/2003 | Bonutti |
| 6,509,659 B1 | 1/2003 | Carroll et al. |
| 6,572,571 B2 | 6/2003 | Lowe |
| 6,575,926 B2 | 6/2003 | Bonutti |
| 6,599,255 B2 | 7/2003 | Zhang |
| 6,599,263 B1 | 7/2003 | Bonutti et al. |
| 6,637,429 B2 | 10/2003 | Mundrick et al. |
| 6,682,497 B2 | 1/2004 | Jensen et al. |
| 6,743,187 B2 | 6/2004 | Solomon et al. |
| 6,770,047 B2 | 8/2004 | Bonutti |
| 6,890,285 B2 | 5/2005 | Rahman et al. |
| 6,921,377 B2 | 7/2005 | Bonutti |
| 6,929,616 B2 | 8/2005 | Bonutti et al. |
| 6,958,048 B2 | 10/2005 | Bonutti |
| 6,974,431 B2 | 12/2005 | Jensen et al. |
| 7,044,925 B2 | 5/2006 | Castillo et al. |
| 7,112,179 B2 | 9/2006 | Bonutti et al. |
| 7,182,738 B2 | 2/2007 | Bonutti et al. |
| 7,204,814 B2 | 4/2007 | Peles |
| 7,306,573 B2 | 12/2007 | Bonutti |
| 7,404,804 B2 | 7/2008 | Bonutti |
| 7,473,234 B1 | 1/2009 | Weltner et al. |
| 7,517,330 B2 | 4/2009 | Deharde et al. |
| 8,920,346 B2 | 12/2014 | Bonutti et al. |
| 2001/0047209 A1 | 11/2001 | Solomon et al. |
| 2002/0029784 A1 | 3/2002 | Stark et al. |
| 2002/0183655 A1 | 12/2002 | Zhang |
| 2004/0082885 A1 | 4/2004 | Culhane et al. |
| 2004/0153010 A1 | 8/2004 | Bonutti et al. |
| 2004/0215120 A1 | 10/2004 | Jensen et al. |
| 2005/0197605 A1 | 9/2005 | Bonutti et al. |
| 2006/0036205 A1 | 2/2006 | Bonutti |
| 2007/0038161 A1 | 2/2007 | Bonutti et al. |

(56) References Cited

U.S. PATENT DOCUMENTS

| | | |
|---|---|---|
| 2007/0055190 A1* | 3/2007 | Bonutti .......... A61F 5/0102 602/16 |
| 2007/0100267 A1 | 5/2007 | Bonutti et al. |
| 2007/0135738 A1 | 6/2007 | Bonutti et al. |
| 2007/0197605 A1 | 8/2007 | Glombik et al. |
| 2007/0219475 A1* | 9/2007 | Bonutti .......... A61F 5/0127 602/16 |
| 2007/0219476 A1 | 9/2007 | Bonutti et al. |
| 2008/0091132 A1 | 4/2008 | Bonutti |
| 2008/0188356 A1 | 8/2008 | Bonutti et al. |

FOREIGN PATENT DOCUMENTS

| | | |
|---|---|---|
| DE | 405327 | 10/1924 |
| DE | 2829562 A1 | 7/1978 |
| DE | 8806231 U | 6/1988 |
| EP | 0 181 668 A1 | 5/1986 |
| EP | 0 181 688 A2 | 5/1986 |
| EP | 0 380 060 A2 | 8/1990 |
| EP | 0 510 840 A1 | 10/1992 |
| FR | 2661333 A1 | 10/1991 |
| JP | 4261657 | 9/1992 |
| JP | 2001087296 | 4/2001 |
| SU | 1158195 A | 5/1985 |
| SU | 1426580 A1 | 2/1987 |
| SU | 1671296 A1 | 8/1991 |
| WO | 88/04543 | 6/1988 |
| WO | 2004/073143 A1 | 8/2004 |
| WO | 2005086741 A2 | 9/2005 |
| WO | 2007/051168 A2 | 5/2007 |
| WO | 2007/109638 A2 | 9/2007 |
| WO | 2008/036895 A2 | 3/2008 |

OTHER PUBLICATIONS

Smith & Nephew DonJoy Inc., Quadrant Brace Specifications, http://www.shoulder.com/quadspec.html, Jun. 5, 1998, 1 page.
Smith & Nephew DonJoy Inc., Ultrasling, http://www.shoulder.com/ultra.html, Jun. 5, 1998, 1 page.
Neporent et al., Weight Training for Dummies, IDG Books Worldwide, Inc. (1997), 3 pages.
Practitioner Information for Dynasplint LPS Orthosis—Knee Extension, Dynasplint Systems Inc., (No date available), 6 pages.
Taber's Cyclopedic Medical Dictionary, 16th Edition, pp. 520-521 (No date available).
UE Tech—Technology Meeting Human Needs, Rehabilitation Product Catalog, vol. 7, (No date available), 28 pages.

* cited by examiner

KNEE ORTHOSIS

CROSS-REFERENCE TO RELATED APPLICATION

The present application claims the benefit of U.S. Provisional Patent Application No. 60/888,107 filed Feb. 5, 2007, entitled KNEE ORTHOSIS, the contents of which are herein incorporated by references in its entirety.

FIELD OF THE INVENTION

The present invention relates to an adjustable orthosis for stretching tissue in the human body. In particular, the present invention relates to an adjustable orthosis which can be used for stretching tissue such as ligaments, tendons or muscles around a joint during flexion or extension of the joint.

BACKGROUND OF THE INVENTION

In a joint, the range of motion depends upon the anatomy of that joint and on the particular genetics of each individual. Typically, joints move in two directions, flexion and extension. Flexion is to bend the joint and extension is to straighten the joint; however, in the orthopedic convention some joints only flex. For example, the ankle has dorsiflexion and plantarflexion. Other joints not only flex and extend, they rotate. For example, the elbow joint has supination and pronation, which is rotation of the hand about the longitudinal axis of the forearm placing the palm up or the palm down.

When a joint is injured either by trauma or by surgery, scar tissue can form, often resulting in flexion or extension contractures. Such conditions can limit the range of motion of the joint, limiting flexion (in the case of an extension contracture) or extension (in the case of a flexion contracture) of the injured joint. It is often possible to correct this condition by use of a range-of-motion (ROM) orthosis.

ROM orthoses are devices commonly used during physical rehabilitative therapy to increase the range-of-motion over which the patient can flex or extend the joint. Commercially available ROM orthoses are typically attached on opposite members of the joint and apply a torque to rotate the joint in opposition to the contraction. The force is gradually increased to increase the working range or angle of joint motion. Exemplary orthoses include U.S. Pat. No. 7,112,179, entitled "Orthosis;" U.S. Pat. No. 6,599,263, entitled "Shoulder Orthosis;" U.S. Pat. No. 6,113,562, entitled "Shoulder Orthosis;" U.S. Pat. No. 5,848,979, entitled "Orthosis;" U.S. Pat. No. 5,685,830, entitled "Adjustable Orthosis Having One-Piece Connector Section for Flexing;" U.S. Pat. No. 5,611,764, entitled "Method of Increasing Range of Motion;" U.S. Pat. No. 5,503,619, entitled "Orthosis for Bending Wrists;" U.S. Pat. No. 5,456,268, entitled "Adjustable Orthosis;" U.S. Pat. No. 5,453,075, entitled "Orthosis with Distraction through Range of Motion;" U.S. Pat. No. 5,395,303, entitled "Orthosis with Distraction through Range of Motion;" U.S. Pat. No. 5,365,947, entitled "Adjustable Orthosis;" U.S. Pat. No. 5,285,773, entitled "Orthosis with Distraction through Range of Motion;" U.S. Pat. No. 5,213,095, entitled "Orthosis with Joint Distraction;" and U.S. Pat. No. 5,167,612, entitled "Adjustable Orthosis," all to Bonutti and herein are expressly incorporated by reference in their entirety.

SUMMARY OF THE INVENTION

The present invention provides an orthosis for stretching tissue around a joint of a patient between first and second relatively pivotable body portions. The joint and the first and second body portions define on one side of the joint an inner sector which decreases in angle as the joint is flexed and define on the opposite side of the joint an outer sector which decreases in angle as the joint is extended.

The orthosis includes a first arm member affixable to the first body portion. The first arm member has a first extension member extending therefrom. A second arm member affixable to the second body portion is also included. The second arm member has a second extension member having an arcuate shape extending therefrom. A third arm member including a third extension member, having an arcuate shape extending therefrom, is interposed between the first and second arm members. The second and third arm members are operatively connected, such that the second arm member travels along an arcuate path defined by the second extension member when the second arm member is moved from a first position to a second position relative to the third arm member. The first arm member is slidingly connected to the third extension member, such that the third arm member slides along an arcuate path defined by the third extension member when the third arm member is moved from the first position to the second position relative to the first arm member.

The orthosis further includes a drive assembly for selectively moving the second arm member relative to the first and third arm members. The drive assembly is mounted onto the third arm member, engaging the second extension member. The drive assembly can be manually or automatically actuated to selectively move the third arm member relative to the second extension member.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 16A shows another embodiment of the first arm member of the orthosis of FIG. 9;

DETAILED DESCRIPTION OF THE INVENTION

The present invention relates to an orthosis for moving a joint between first and second relatively pivotable body portions. The joint and the first and second body portions define on one side (the flexor side) of the joint an inner sector which decreases in angle as the joint is flexed (bent) and on the opposite side (the extensor side) of the joint an outer sector which decreases in angle as the joint is extended (straightened). The orthosis of the present invention is affixable to either the flexor or extensor side of the joint for treatment of flexion or extension contractures.

Figure 1:
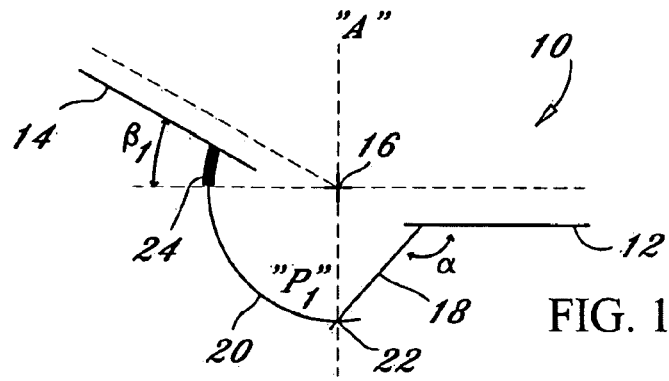
FIG. 1 is a schematic diagram of the orthosis of the present invention in a flexed position.

Referring now to the drawing figures in which like reference designators refer to like elements, there is shown in FIG. 1, a schematic of the orthosis 10 of the present invention. The orthosis 10 includes a first arm member 12 attachable to the first body portion and a second arm member 14 attachable to the second body portion, wherein a joint axis of rotation 16 is interposed between and offset from the first and second arm members 12 and 14. The first and second arm members 12 and 14 are operatively connected to each other offset from the joint axis 16.

The first arm member 12 of the orthosis 10 includes a first extension member 18, which extends at angle α from the first arm member 12. The second arm member 14 of the orthosis 10 includes a second extension member 20 extending therefrom and having an arcuate shape. The first and second extension members 18 and 20 are operatively connected at point "P," such that in operation the second extension member 20 travels along an arcuate path about and substantially through point "P." The arcuate shape of the second extension member 20 results in the second body portion rotating about the joint axis 16, when the second arm member 14 is moved from a first position to a second position relative to the first arm member 12. The angle α between the first extension member 18 and the first arm member 12 and the radius of curvature of the second extension member 20 are a function of the joint to be treated and the degree of flexion or extension contractures.

The orthosis further includes a drive assembly 22 at point "P." The drive assembly connects the first and second extension members 18 and 20 for applying force to the first and second arm members 12 and 14 to pivot the first and second body portions relative to each other about the joint.

Figure 2:
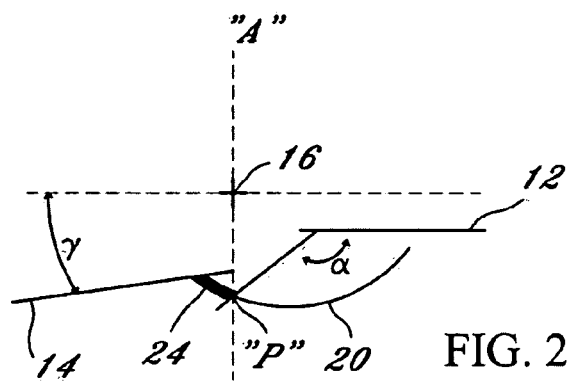
FIG. 2 is a schematic diagram of the orthosis of the present invention in an extended position.

The orthosis 10 of the present invention is shown having an angle α such that the operative connection, at point "P," of the first and second extensions 18 and 20 is located in a plane "A" passing through the joint axis 16, wherein plane "A" is substantially orthogonal to a longitudinal axis of the first arm member 12. This position of point "P" provides an angle $\beta_1$ between the second arm member 14 and the joint axis 16, wherein $\beta_1$ is the maximum angle of flexion. As shown in FIG. 2, the second extension member includes a stop 24. The stop 24 acts to limit the angle of maximum extension γ between the second arm member 14 and the joint axis 16. An increase in the length of the stop 24 will decrease the angle of maximum extension γ. A decrease in the length of the stop 24 will increase the angle of maximum extension γ.

Figure 3:
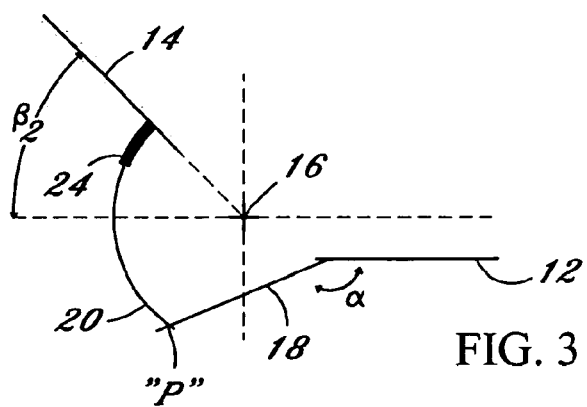
FIG. 3 is a second schematic diagram of the orthosis of the present invention in a flexed position.

Referring to FIG. 3, the maximum flexion angle can be increased by increasing the angle α. An increase in the angle α will move the point "P" to a location "in front of" the plane "A." This position of point "P" provides an angle $\beta_2$ between the second arm member 14 and the joint axis 16 in maximum flexion, wherein $\beta_2$ is greater than $\beta_1$. The greater the angle α, the greater the angle of maximum flexion.

Alternatively, (not shown) a decrease in the angle α will move the point "P" to a location "behind" the plane "A." This position of point "P" provides an angle $\beta_3$ between the second arm member 14 and the joint axis 16 in maximum flexion, wherein $\beta_3$ is less than $\beta_1$. The smaller the angle α, the smaller the angle β of maximum flexion.

Figure 4:
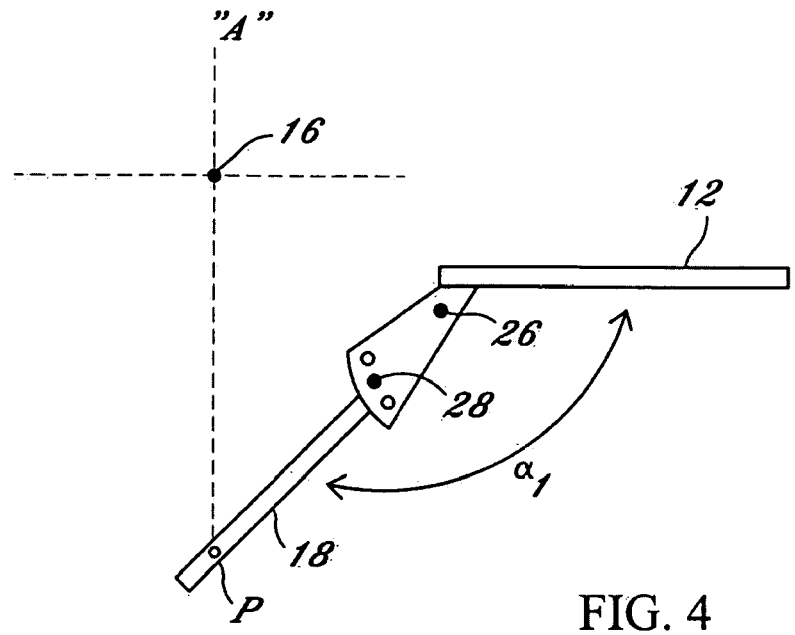
FIG. 4 shows an adjustable first extension member of the orthosis of the present invention.

Referring to FIG. 4, the first extension member 18 is selectively, pivotally connected at location 26 to the first arm member 12. The pivotal connection 26 of the first extension member 18 permits the angle α between the first extension member 18 and the first arm member 12 to be selectively increased and decreased, increasing and decreasing the range of motion. In a first position 28, the first extension member 18 is positioned at an angle $\alpha_1$, wherein the operative connection, at point "P," of the first and second extension members 18 and 20 is located in a plane "A" passing through the joint axis 16, wherein plane "A" is substantially orthogonal to a longitudinal axis of the first arm member 12. The first position 28 of point "P" provides a maximum angle of flexion of $\beta_1$. The second extension member stop 24 acts to limit the angle of maximum extension $\gamma_1$ between the second arm member 14 and the joint axis 16.

Figure 5:
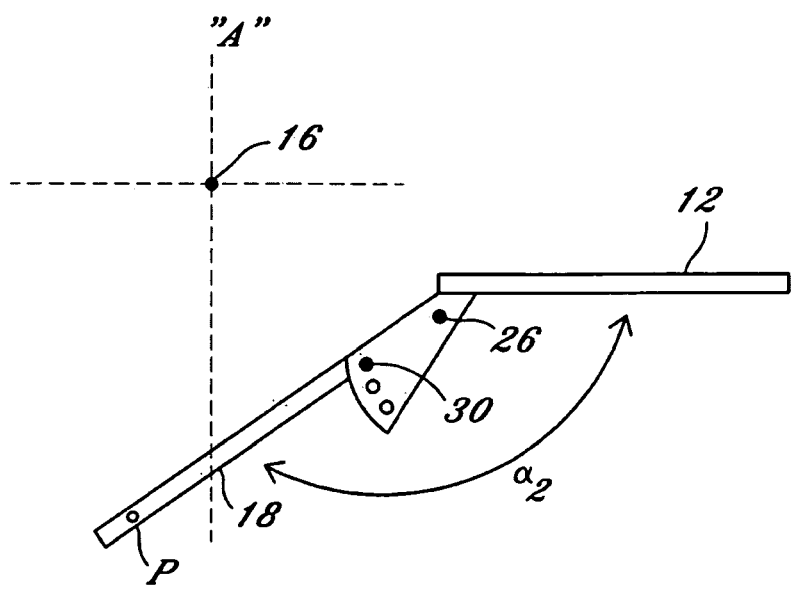
FIG. 5 shows the adjustable first extension member of FIG. 4 in a second position.

Referring to FIG. 5, in a second position 30 the angle α is increased to an angle $\alpha_2$, positioning the point "P" to a location "in front of" the plane "A." The second position 30 of point "P" provides a maximum angle of flexion of $\beta_2$, wherein $\beta_2$ is greater than $\beta_1$. The second extension member stop 24 acts to limit the angle of maximum extension $\gamma_2$ between the second arm member 14 and the joint axis, wherein $\gamma_2$ is less the $\gamma_1$.

The selective pivotal connection 26 of the first extension member 18 to the first arm member 12 can have a plurality of selectable positions. The angle $\alpha$ between the first arm member 12 and the first extension 18 can be selectively increased to move the point "P", on, "in front of" or "behind" the plane "A." It is also envisioned that a positioned can be selected to increase the angle $\alpha$ between the first arm member 12 and the first extension 18 sufficiently to move the point "P" "in front of" plane "A" and "above" the longitudinal axis of the first arm member 12, maximizing the maximum angle of flexion $\beta$.

The orthosis 10 of the present invention can be connected to the flexor side of the first and second body portions of the joint, which results in a decrease in angle as the joint is flexed (bent) and an increase in angle and the joint is extended (straightened). Alternatively, orthosis 10 of the present invention can be connected to the extensor side of the joint, which results in a decrease in angle as the joint is extended straightened and an increase in angle as the joint is flexed (bent).

Figure 6:
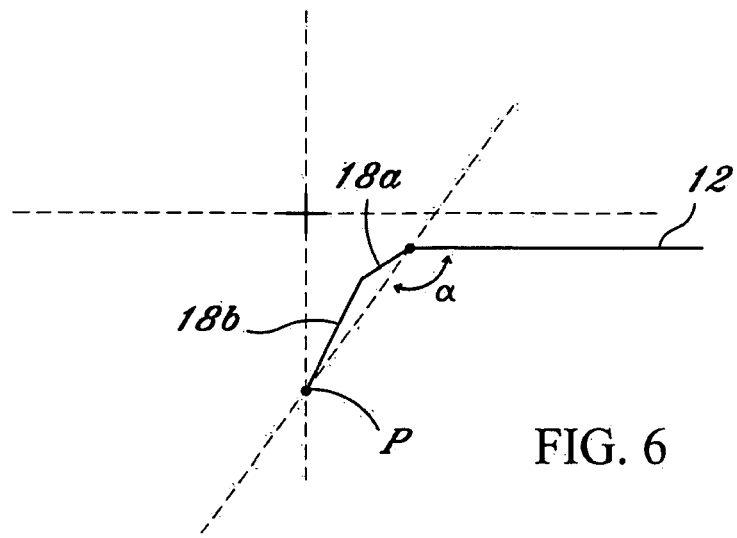
FIG. 6 shows a segmented first extension member of the present invention.
Figure 7:
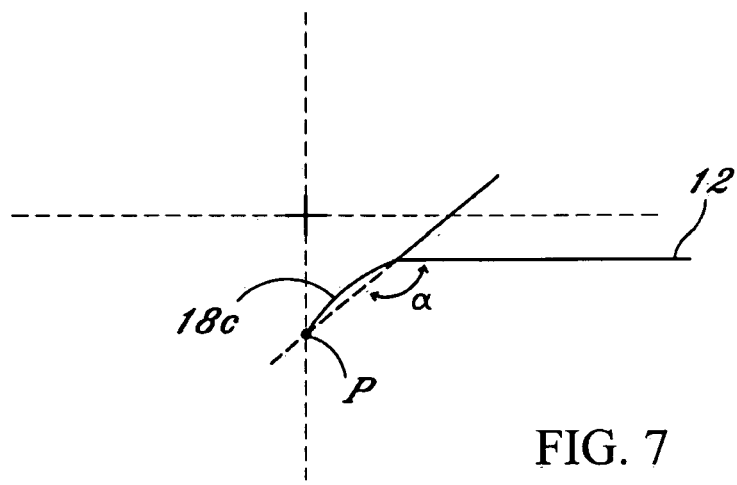
FIG. 7 shows an arcuate first extension member of the present invention.

The previous description of the first arm member 12 depicts a first extension 18 having a substantially linear shape, extending at an angle $\alpha$ from the first arm member 12. However, it is within the scope of the present invention that the first extension member 18 can be any shape extending from the first arm member 12 which positions the point "P" in the desired relationship to the plane "A." Referring to FIG. 6, a segmented first extension member is shown, including a first extension member segment 18a and a second extension member segment 18b. The first and second extension member segments 18a and 18b extend from the first arm member 12, positioning the point "P" at an angle $\alpha$ from the first arm member 12. Referring to FIG. 7, an arcuate first extension member 18c is shown. The arcuate extension member 18c extends from the first arm member 12, positioning the point "P" at an angle $\alpha$ from the first arm member 12.

Figure 8:
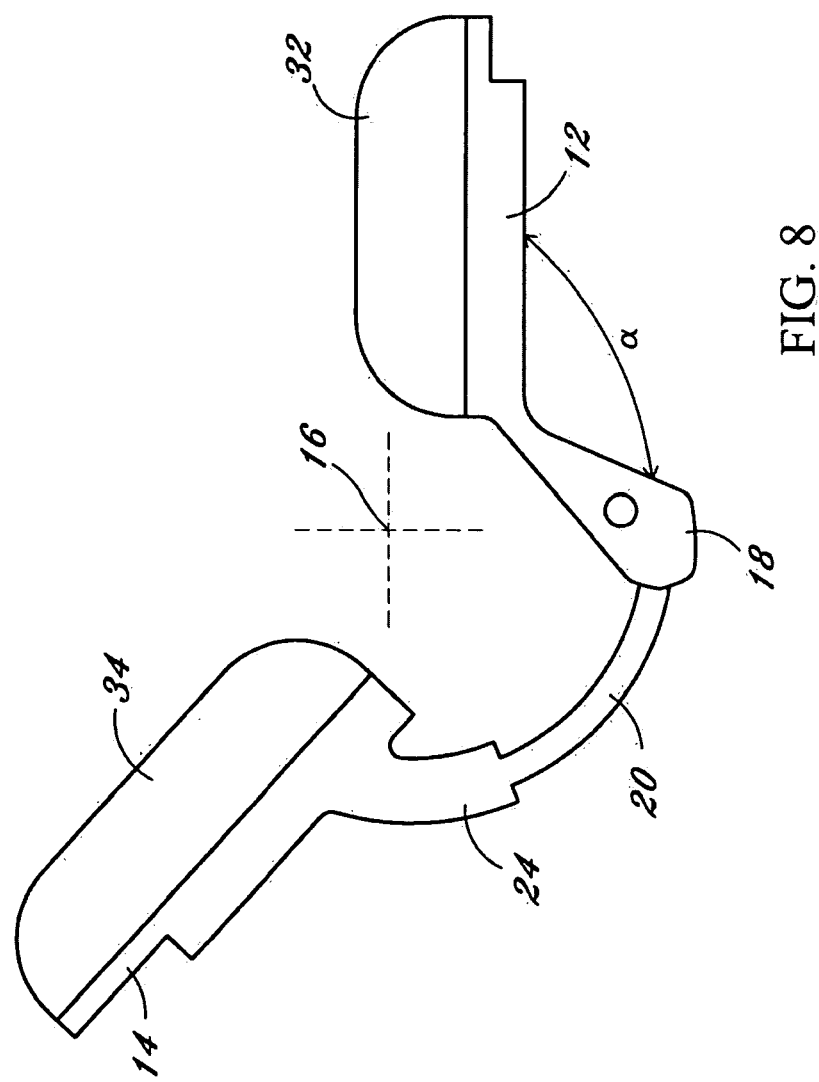
FIG. 8 shows an orthosis of the present invention.

Referring to FIG. 8, the orthosis 10 of the present invention includes a first arm member 12 attachable to the first body portion and a second arm member 14 attachable to the second body portion, wherein the joint axis 16 is interposed between and offset from the first and second arm members 12 and 14. The first and second arm members 12 and 14 are connected with each other offset from the joint axis 16.

The first arm member 12 of the orthosis 10 includes a first extension member 18, which extends at angle $\alpha$ from the first arm member 12. The second arm member 14 of the orthosis 10 includes a second extension member 20, having an arcuate shape. The first and second extension members 18 and 20 are operatively connected a point "P," such that in operation the second extension member 20 travels along an arcuate path about and substantially through point "P." The arcuate shape of the second extension member 20 results in the second body portion rotating about the joint axis 16, when the second arm member 14 is moved from a first position to a second position relative to the first arm member 12. The angle $\alpha$ between the first extension member 18 and the first arm member 12 and the radius of curvature of the second extension member 20 are a function of the joint to be treated and the degree of flexion or extension contractures.

A first cuff 32 is attached to the first arm member 12, wherein the first cuff 32 is positionable about the first body portion. The first cuff 32 is attached to the first body portion by cuff straps. The first cuff 32 secures the first body portion to the first arm member 12. A second cuff 34 is attached to the second arm member 14, wherein the second cuff 34 is positionable about the second body portion. The second cuff 34 is attached to the second body portion by cuff straps. The second cuff 34 secures the second body portion to the second arm member 14. (The term "cuff" as used herein means any suitable structure for transmitting the force of the orthosis 10 to the limb portion it engages.)

In an exemplary use, the orthosis 10 is operated to extend a joint in the following manner. The first cuff 32 is fastened about the first body portion tightly enough that the first arm member 12 may apply torque to the first body portion without having the first cuff 32 slide along the first body portion. Similarly, the second cuff 34 is fastened securely around the second body portion so that the second arm member 14 may apply torque to the second body portion without the second cuff 34 sliding along the second body portion. The orthosis 10 is attached to the first and second body portions in a first position. The second arm member 14 is rotated from the first position to a second position, relative to the first arm member 12, rotating the second body portion about the joint axis 16 stretching the joint. As the second arm member 14 is rotated to the second position, the second extension member 20 travels along an arcuate path about and substantially through point "P." The orthosis 10 is maintained in the second position for a predetermined treatment time providing a constant stretch to the joint. The orthosis 10 may alternatively be configured to impart a constant force or load on the joint or may utilize the techniques of Static Progressive Stretch. These techniques can be used independent of each or combined, as described in co-pending application Ser. No. 11/203,516, entitled "Range of Motion System and Method", and filed on Aug. 12, 2005, the entirety of which is incorporated by reference.

Additionally, the second extension member 12 can be made of a substantially rigid but flexible material, such that while the second extension member 12 is in the second position, the second extension member 12 acts like a spring, providing dynamic stretch to the connective tissue of the joint.

After the expiration of the treatment time, the second arm member 14 is moved back to the first position, relieving the joint. Optionally, the second arm member 14 can be rotated to a third position, increasing the stretch on the joint. The second arm member 14 can be rotated at discrete time intervals to incrementally increase the stretch of the joint through the treatment cycle. After completion of the treatment cycle, the second arm member is returned to the first position for removal of the orthosis 10.

The first and second arm members 12 and 14 are rigid members made of, for example, aluminum, stainless steel, polymeric, or composite materials. The arms are rigid so as to be able to transmit the necessary forces. It should be understood that any material of sufficient rigidity can be used.

In an embodiment, the components of the orthosis 10 of the present invention are made by injection molding. Generally for injection molding, tool and die metal molds of the orthosis 10 components are prepared. Hot, melted plastic material is injected into the molds. The plastic is allowed to cool, forming components. The components are removed from the molds and assembled. The cuff portions 32 or 34 can be individual molded and attached to the arm members 12 or 14. Alternatively, the cuff portions can be molded as an integrated part of the arm members 12 or 14.

In use, the orthosis 10 can be connected to the flexor side of the first and second body portions of the joint, which results in a decrease in angle as the joint is flexed (bent) and an increase in angle as the joint is extended (straightened). Alternatively, orthosis 10 of the present invention can be connected to the extensor side of the joint, which results in a decrease in angle as the joint is extended straightened and an increase in angle as the joint is flexed (bent).

In an embodiment, the orthosis 10 includes a first cuff 32 for attachment to a first body portion, and a second cuff 34 for attachment to a second body portion. The first body portion is joined to the second body portion at a joint, around which is located, as is well known, soft tissue. Each of the first and second cuffs 32 and 34 includes loop connectors for receiving straps extending around the body portions to clamp the cuffs 32 and 34 to the body portions.

The first cuff 32 is mounted for sliding movement on the first arm member 12 and is slidable along the first arm member 12 in a manner as described below. The second cuff 34 is mounted for sliding movement on a second arm member 14 and is slidable along the second arm member 12 in a manner as described below.

Bending a Joint in Extension:

In operation of the orthosis 10 to extend the joint, the orthosis 10 starts at a more flexed position. The first and second cuffs 32 and 34 are clamped onto the first and second body portions, respectively, by straps, tightly enough so that the cuffs 32 and 34 can apply torque to the body portions to extend the joint. The second arm member 14 is rotated from the first position to a second position, relative to the first arm member 12, rotating the second body portion about the joint axis 16 stretching the joint. As the second arm member 14 is rotated to the second position the second extension member 20 travels along an arcuate path about and substantially through point "P." The orthosis 10 is maintained in the second position for a predetermined treatment time providing a constant stretch to the joint.

As the orthosis 10 is rotated from the first position to the second position, extending the joint, the first and second cuffs 32 and 34 move along the first and second arm members 12 and 14. The first cuff 32 moves inwardly along the first arm member 12. Similarly, the second cuff 34 moves inwardly along the second arm member 14. Because the cuffs 32 and 34 are clamped onto the first and second body portions as described above, the outward pivoting movement of the first and second arm members 12 and 14 and the cuffs 32 and 34 causes the joint to be extended as desired. However, this extension of the joint can place strong distractive forces on the soft tissues around the joint. The sliding movement of the cuffs 32 and 34, inwardly along the first and second arm members 12 and 14, helps to limit these distractive forces by counteracting the outward movement of the first and second arm members 12 and 14. The cuffs 32 and 34 slide inwardly along the first and second arm members 12 and 14 a distance far enough so that the joint is only slightly distracted during extension. Thus, the detrimental effects of strong distractive forces normally generated in forced extension of a joint are avoided, being replaced with the beneficial effects of limited and controlled distraction.

Bending a Joint in Flexion:

In operation of the orthosis 10 to flex the joint, the orthosis 10 starts at a more extended position. The first and second cuffs 32 and 34 are clamped onto the first and second body portions, respectively, by straps, tightly enough so that the cuffs 32 and 34 can apply torque to the body portions to extend the joint. The second arm member 14 is rotated from the first position to a second position, relative to the first arm member 12, rotating the second body portion about the joint axis 16 stretching the joint. As the second arm member 14 is rotated to the second position the second extension member 20 travels about and substantially though point "P," along an arcuate path. The orthosis 10 is maintained in the second position for a predetermined treatment time providing a constant stretch to the joint.

As the orthosis 10 is rotated from the first position to the second position, flexing the joint, the first and second cuffs 32 and 34 move along the first and second arm members 12 and 14. The first cuff 32 moves outwardly along the first arm member 12. Similarly, the second cuff 34 moves outwardly along the second arm member 14. Because the cuffs 32 and 34 are clamped onto the first and second body portions the inward pivoting movement of the first and second arm members 12 and 14 and the cuffs 32 and 34 causes the joint to be flexed as desired. However, this flexion of the joint can place strong compressive forces on the soft tissues around the joint. The sliding movement of the cuffs 32 and 34, outwardly along the first and second arm members 12 and 14, helps to limit these compressive forces by counteracting the inward movement of the first and second arm members 12 and 14. The cuffs 32 and 34 slide outwardly along the first and second arm members 12 and 14 a distance far enough so that the joint is only slightly compressed during flexion. Thus, the detrimental effects of strong compressive forces normally generated in forced flexion of a joint are avoided, being replaced with the beneficial effects of limited and controlled compression.

Figure 9:
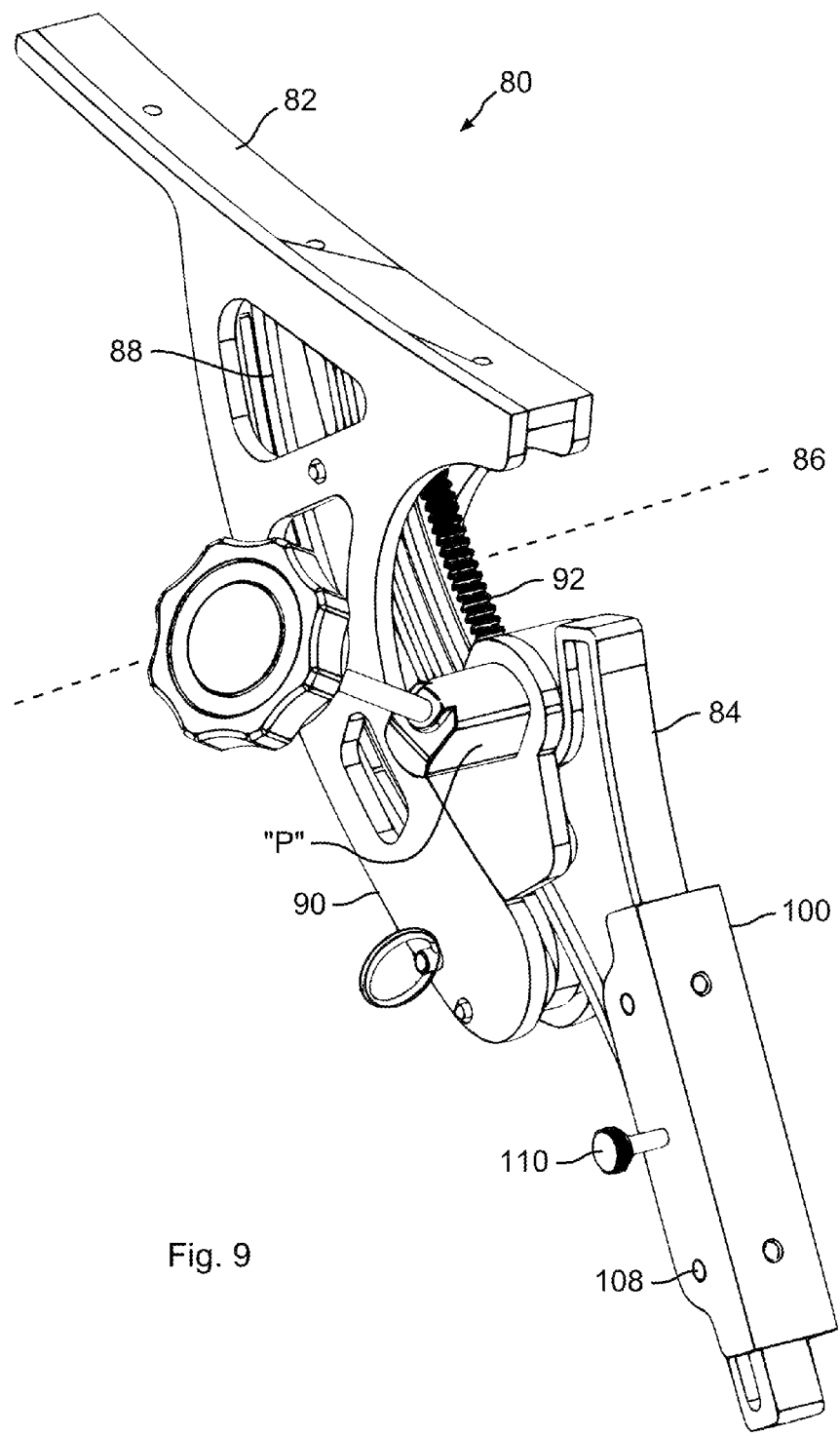
FIG. 9 depicts a perspective view of an orthosis of the present invention for extending a knee joint in a patient with the cuffs removed.
Figure 10:
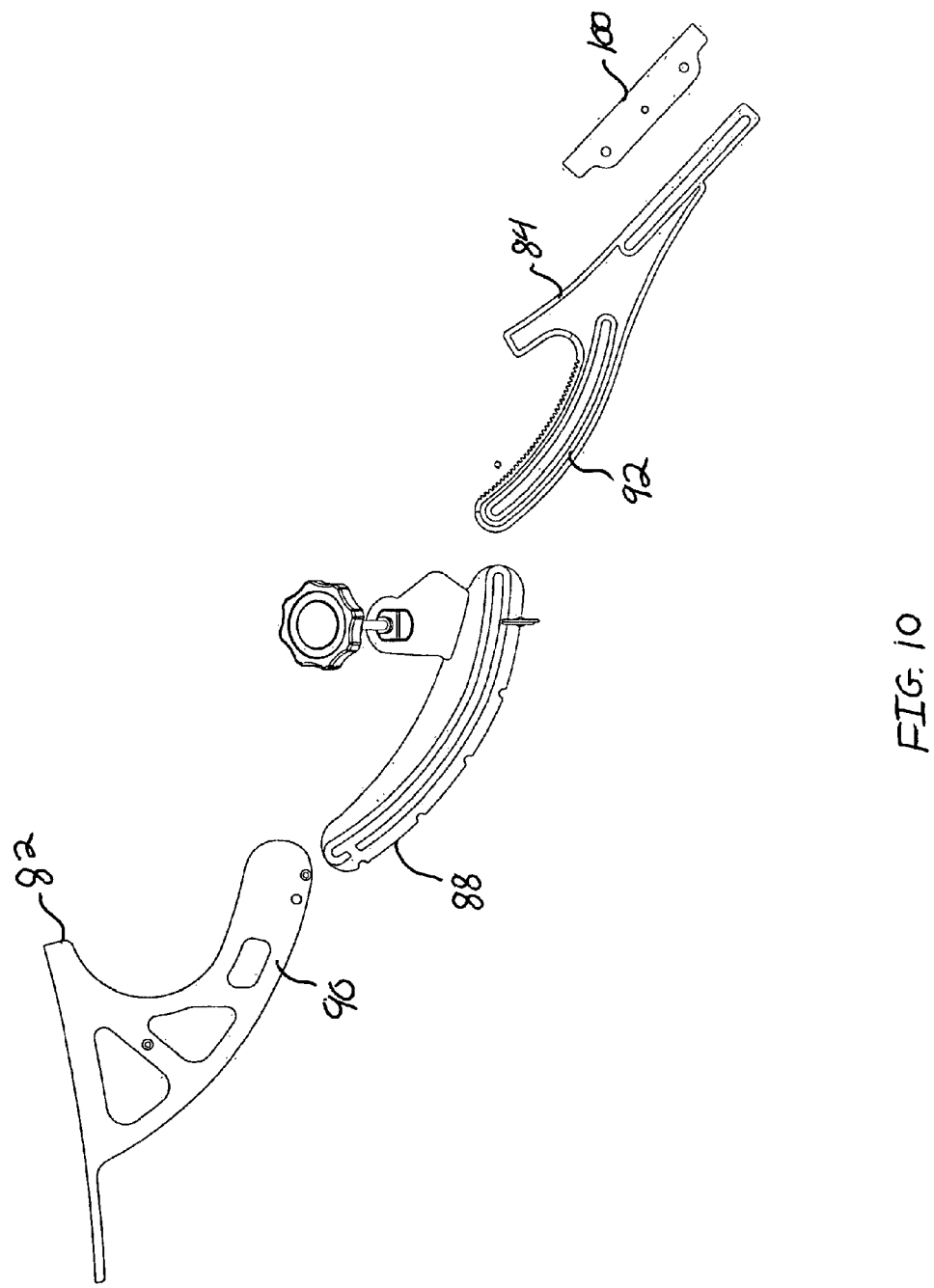
FIG. 10 depicts an exploded side view of the orthosis of FIG. 9.
Figure 10A:
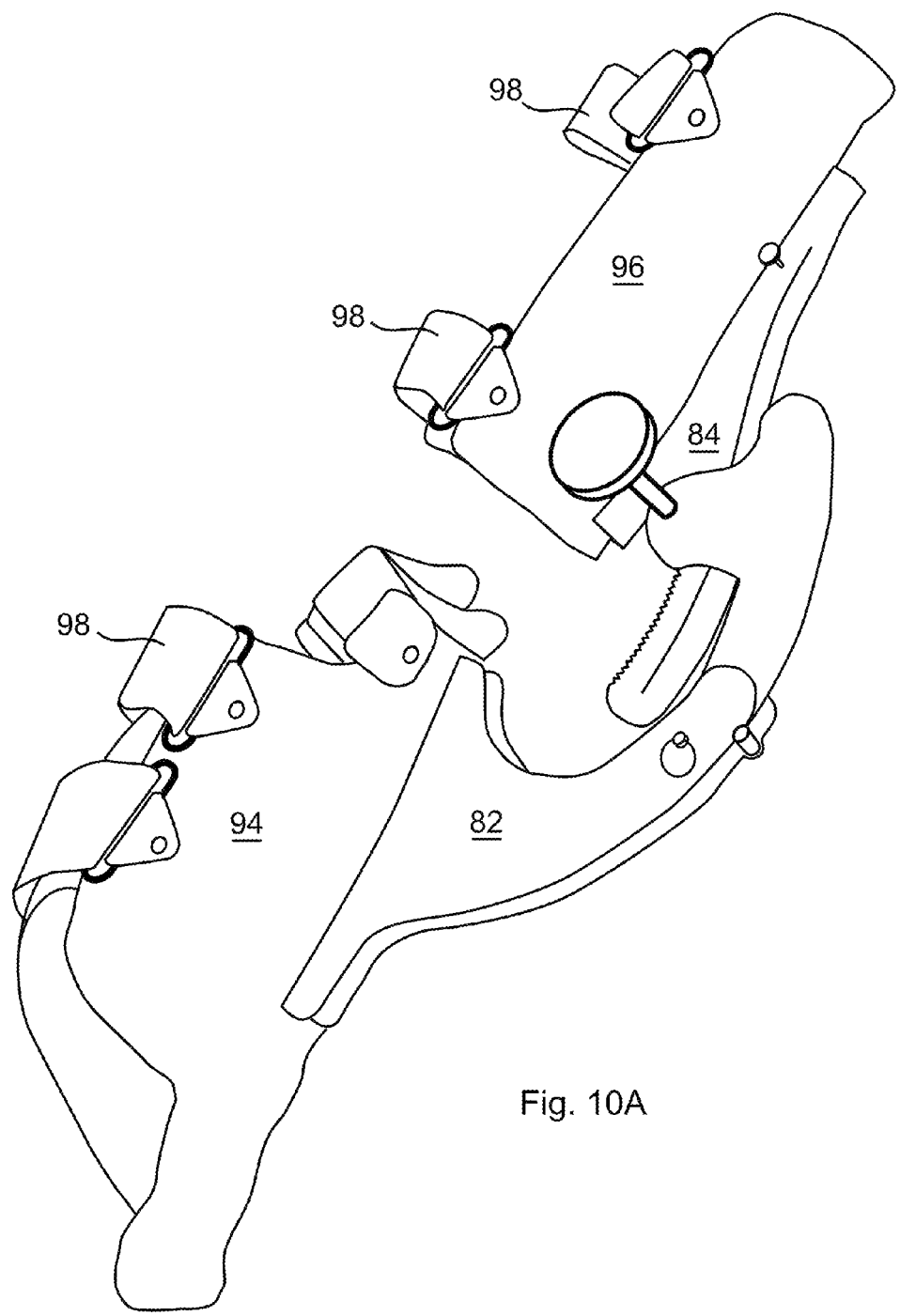
FIG. 10a shows the orthosis of FIG. 9 with first and second cuffs.

Referring to FIGS. 9, 10, and 10a, a knee orthosis 80 of the present invention includes a first arm member 82 attachable to the upper leg portion and a second arm member 84 attachable to the lower leg portion, wherein the joint axis 86 is interposed between and offset from the first and second arm members 82 and 84. A third arm member 88 is interposed between the first and second arm members 82 and 84, where the first and second arm members 82 and 84 are connected to the third arm member 88, offset from the joint axis 86.

The first arm member 82 of the knee orthosis 80 includes a first extension member 90, which extends from the first arm member 82. The second arm member 84 of the knee orthosis 80 includes a second extension member 92 having an arcuate shape. The first and second extension members 90 and 92 are operatively connected to the third arm member 88, where the second extension member 92 is operably connected to the third arm member 88 at a point "P," such that in operation the second arm member 84 travels through the third arm member 88 along an arcuate path of the second extension member 92. The arcuate shape of the second extension member 92 results in the lower leg portion rotating about the joint axis 86, when the second arm member 84 is moved from a first position to a second position relative to the first and third arm members 82 and 88. The radius of curvature of the second extension member 92 is a function of the joint to be treated and the degree of extension contractures.

A first cuff 94 is attached to the first arm member 82, wherein the first cuff 94 is positionable about the upper leg portion. The first cuff 94 is attached to the upper leg portion by cuff straps 98. The first cuff 94 secures the upper leg portion to the first arm member 82. Although the surface of first arm 82 to which first cuff 94 attaches is shown as arcuate (see FIG. 16), this surface can also be substantially straight (see FIG. 16A). This surface of first arm member 82 can also be provided with a widen flat portion of paddle 83 to provide stability in use, resting against the chair or other face. A second cuff 96 is attached to the second arm member 84, wherein the second cuff 96 is positionable about the lower leg portion. The second cuff 96 is attached to the lower leg portion by a cuff straps 98. The second cuff 96 secures the lower leg portion to the second arm member 84. The cuffs 94 and 96 can be provided in a variety of sizes or have adjustable sizes to fit about the body portions. (The term "cuff" as used herein means any suitable structure for transmitting the force of the orthosis 80 to the limb portion it engages).

Figure 11:
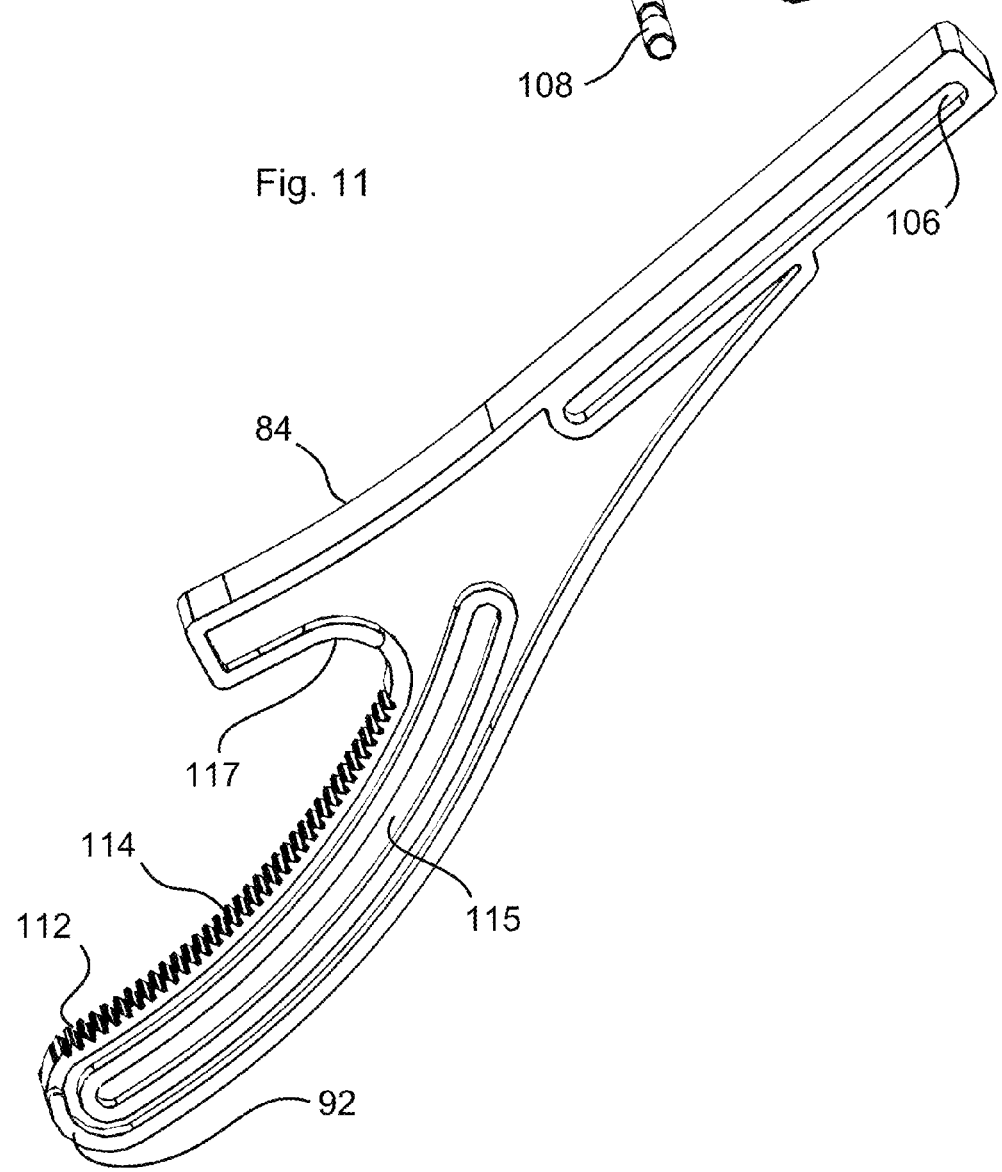
FIG. 11 depicts a side view exploded view of a second arm member of the orthosis of FIG. 9.
Figure 12:
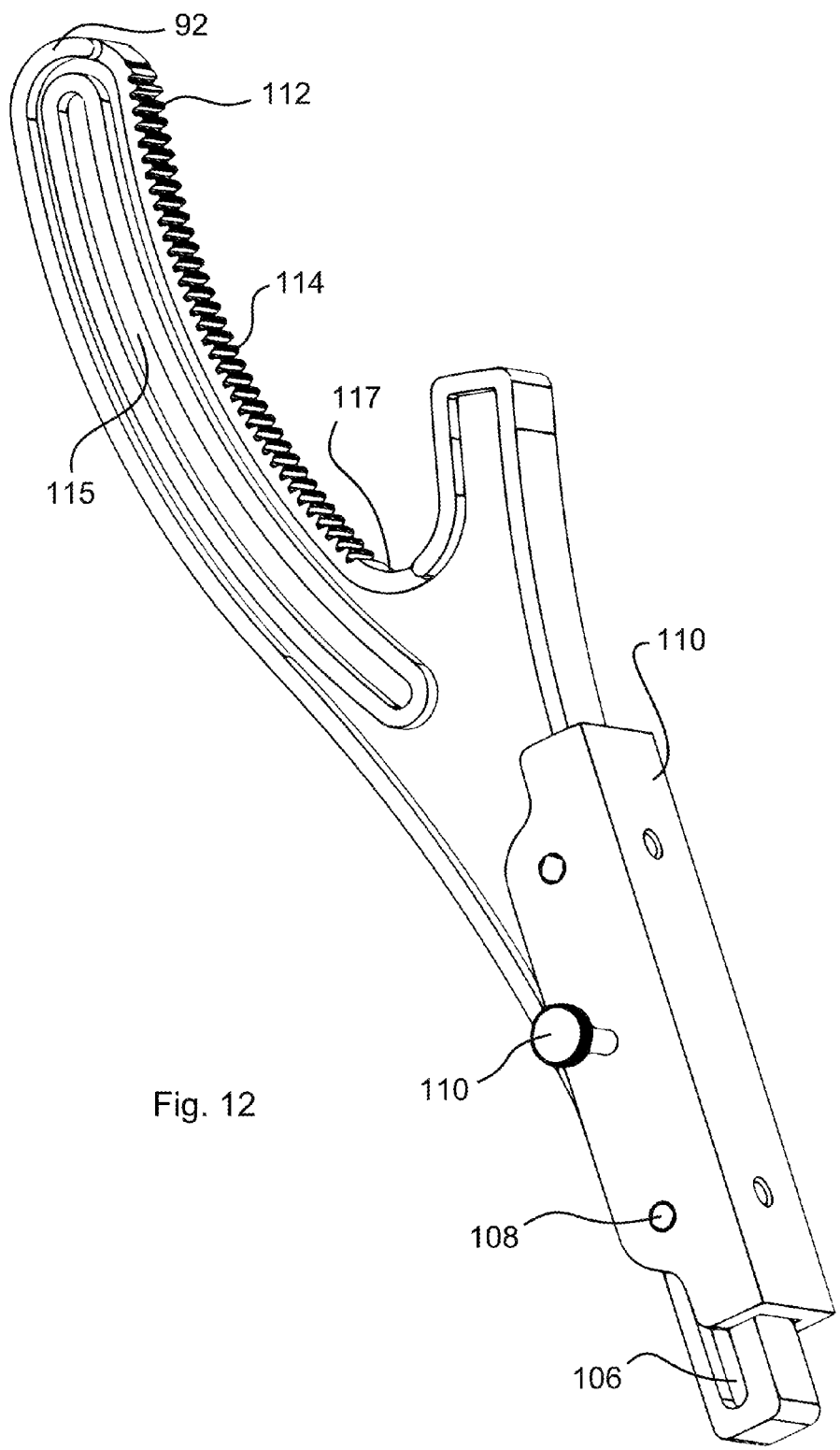
FIG. 12 depicts a second arm member of the orthosis of FIG. 9.

Referring to FIGS. 11 and 12, the second cuff 96 (not shown) can be slidingly connected to the second arm member 84. A sliding bar 100 is affixed to the first cuff 96. The second arm member 84 includes a main channel 106 configured to slidingly receive the sliding bar 100. Pins 108 are positioned though opposite sides of the sliding bar 100 into the channels 106 of the second arm member 84 to slidingly secure the sliding bar 100 in the main channel 106. An adjustable member 110 can be threaded though the first arm member 84, into a channel 106 to adjustably secure the position of the sliding bar 100. As such, the position of the second cuff 96 can be adjusted with respected the second arm member 84, the position being secured with the adjustable member 110. Alternatively, the second cuff 96 can be free to slide with respect to the second arm member 84, thereby allowing the position of the second cuff 96 to self adjust during operation of the knee orthosis 80.

The second extension member 92 has an arcuate shape, where the radius of curvature of the second extension member 92 is a function of the joint to be treated and the degree of extension contractures. The second extension member 92 includes an inner surface 112 have a plurality of teeth 114 thereon, where a stop 117 is provided to limit the travel along the inner surface 112. The second extension member 92 can include channels 115 disposed on opposite sides thereof.

Figure 13:
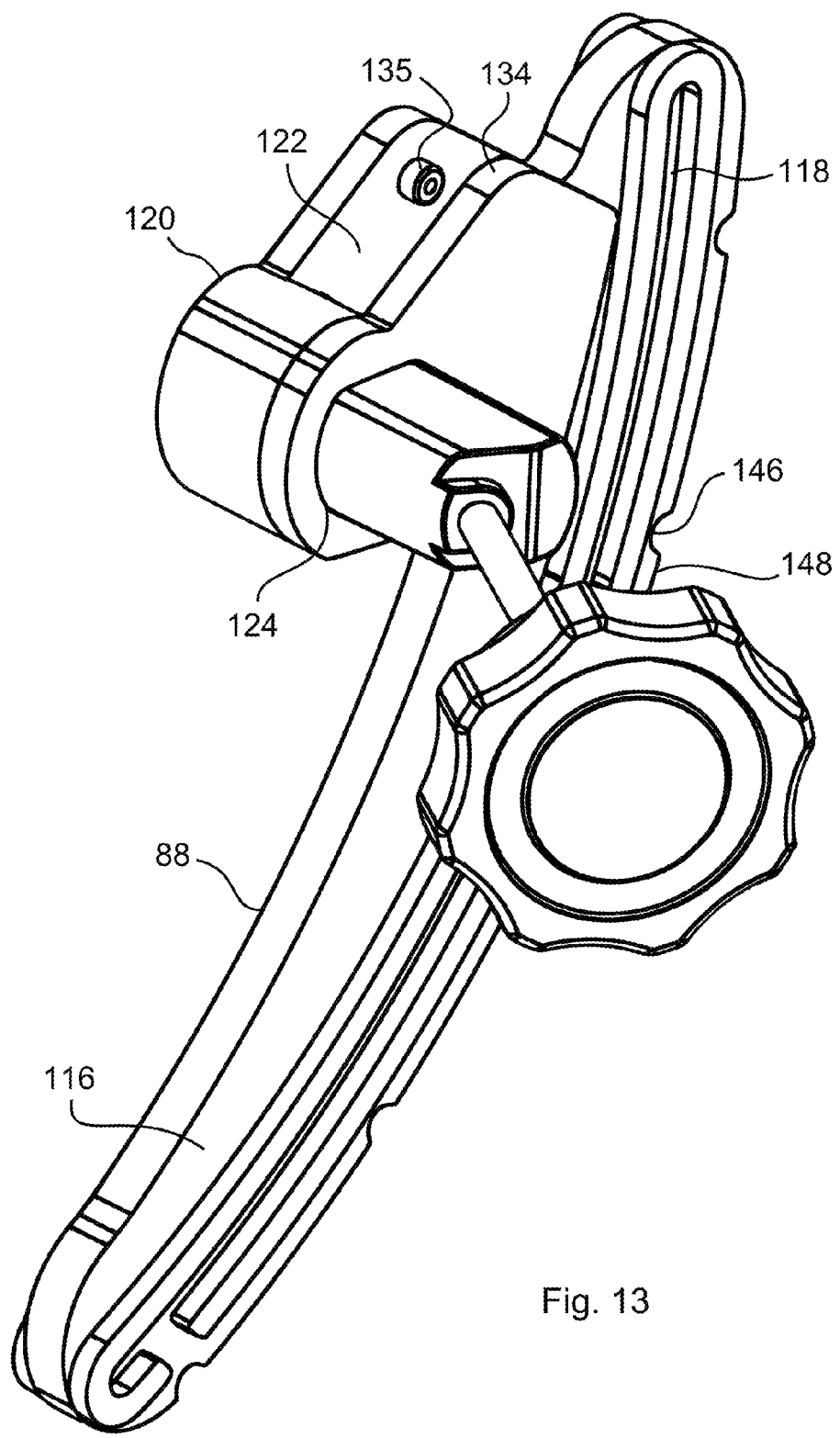
FIG. 13 depicts a third arm member of the orthosis of FIG. 9.

Referring to FIG. 13, the third arm member 88 includes a third extension member 116 having an arcuate shape, where the radius of curvature of the third extension member 116 is a function of the joint to be treated and the degree of extension contractures. The third extension member 116 includes channels 118 disposed on opposite sides thereof. A drive housing 120 is positioned proximal to a guide channel 122, where the drive housing 120 includes a drive assembly 124.

Figure 14:
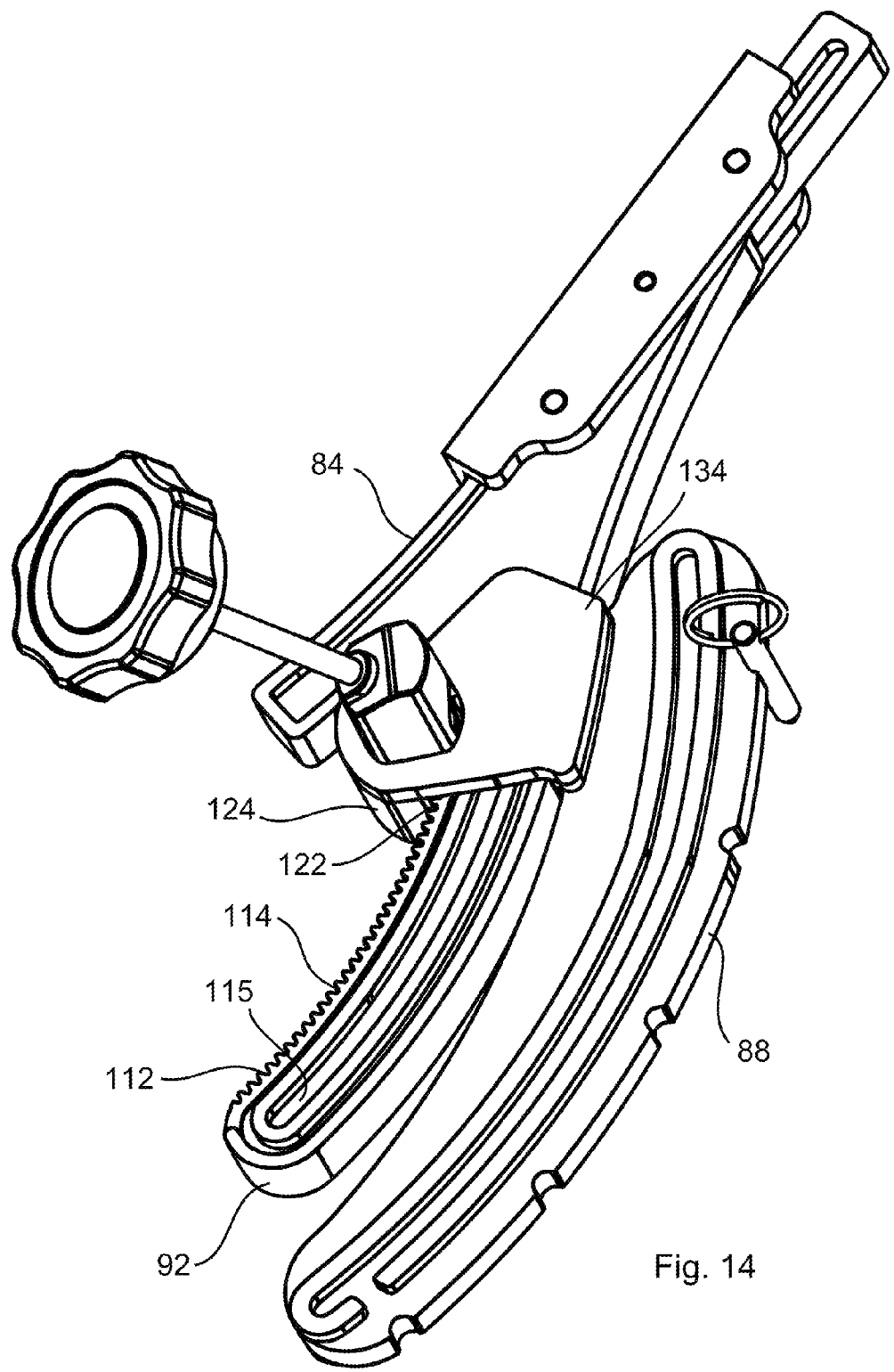
FIG. 14 depicts the second arm member engaging the third arm member of the orthosis of FIG. 9.
Figure 15:
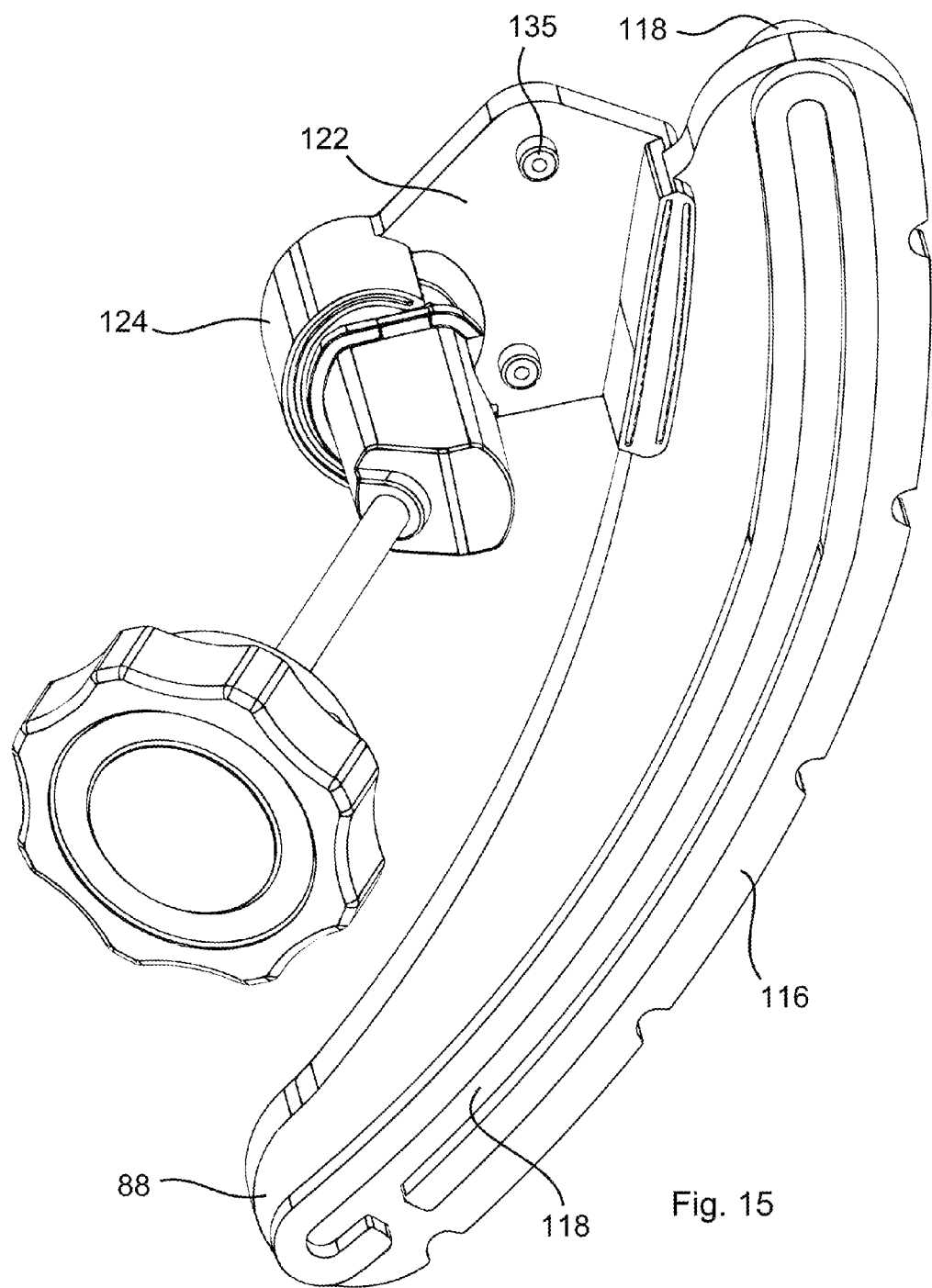
FIG. 15 depicts a partial view of the third arm member of the orthosis of FIG. 9.

Referring also to FIGS. 14 and 15, the second extension member 92 is positioned in the guide channel 122, such that the drive assembly 124 engages the teeth 114 on the inner surface 112 of the second extension member 92. An actuation of the drive assembly 124 drives the second extension member 92 through the guide channel 122. The cover plate 134 is positioned over the guide channel 122, securing the second extension member 92 in the guide channel 122 and defining a passage through which it travels.

Guide pins 135 can be positioned in the channels 115 of the second extension member 92, engaging on one side the third arm member 88 and on an opposite side the cover plate 134. The guide pins 135 can be used to secure the second extension member 92 in the passage and control the tracking of the second arm member 84 along the guide channel 122.

Figure 16:
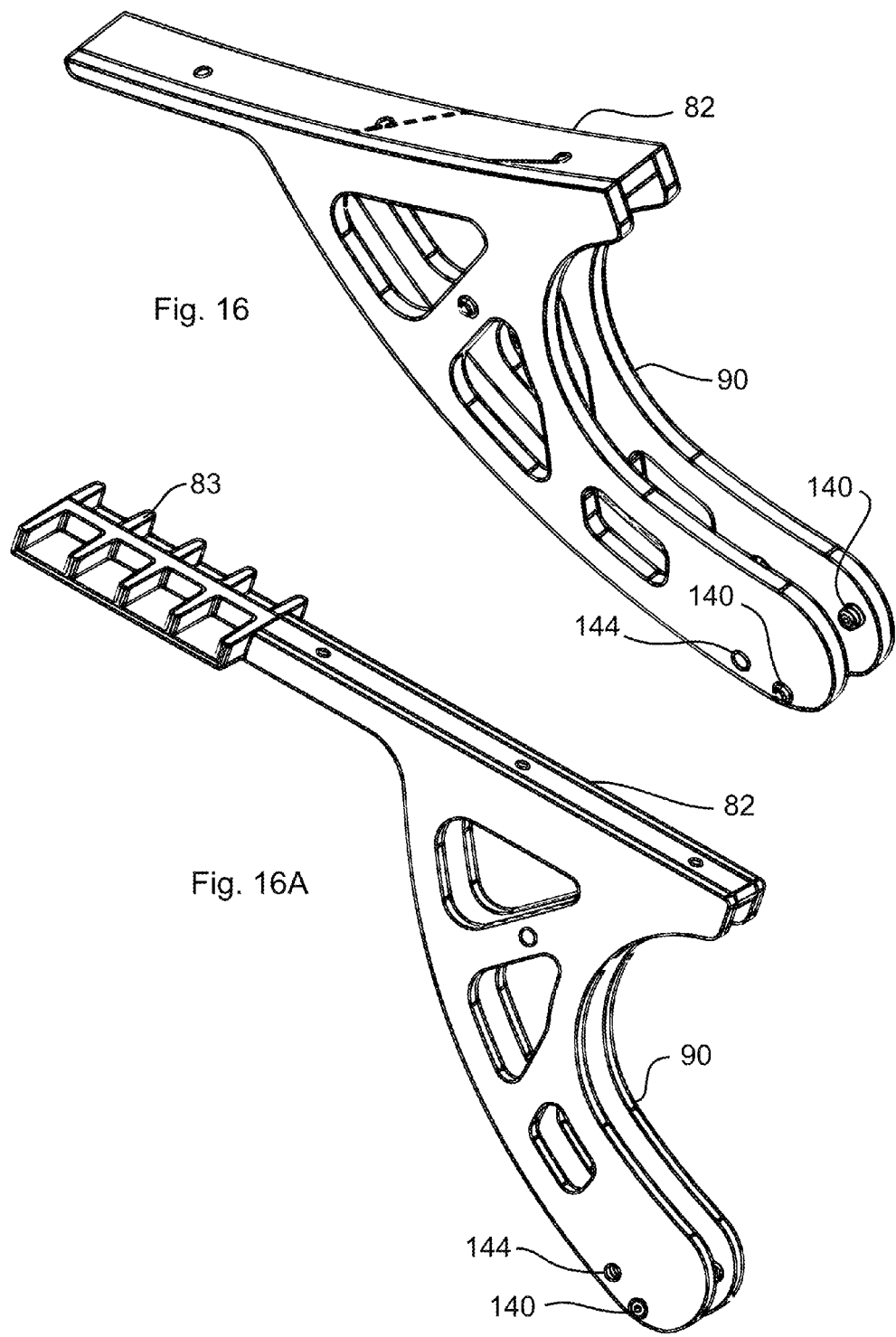
FIG. 16 depicts the first arm member of the orthosis of FIG. 9.
Figure 17:
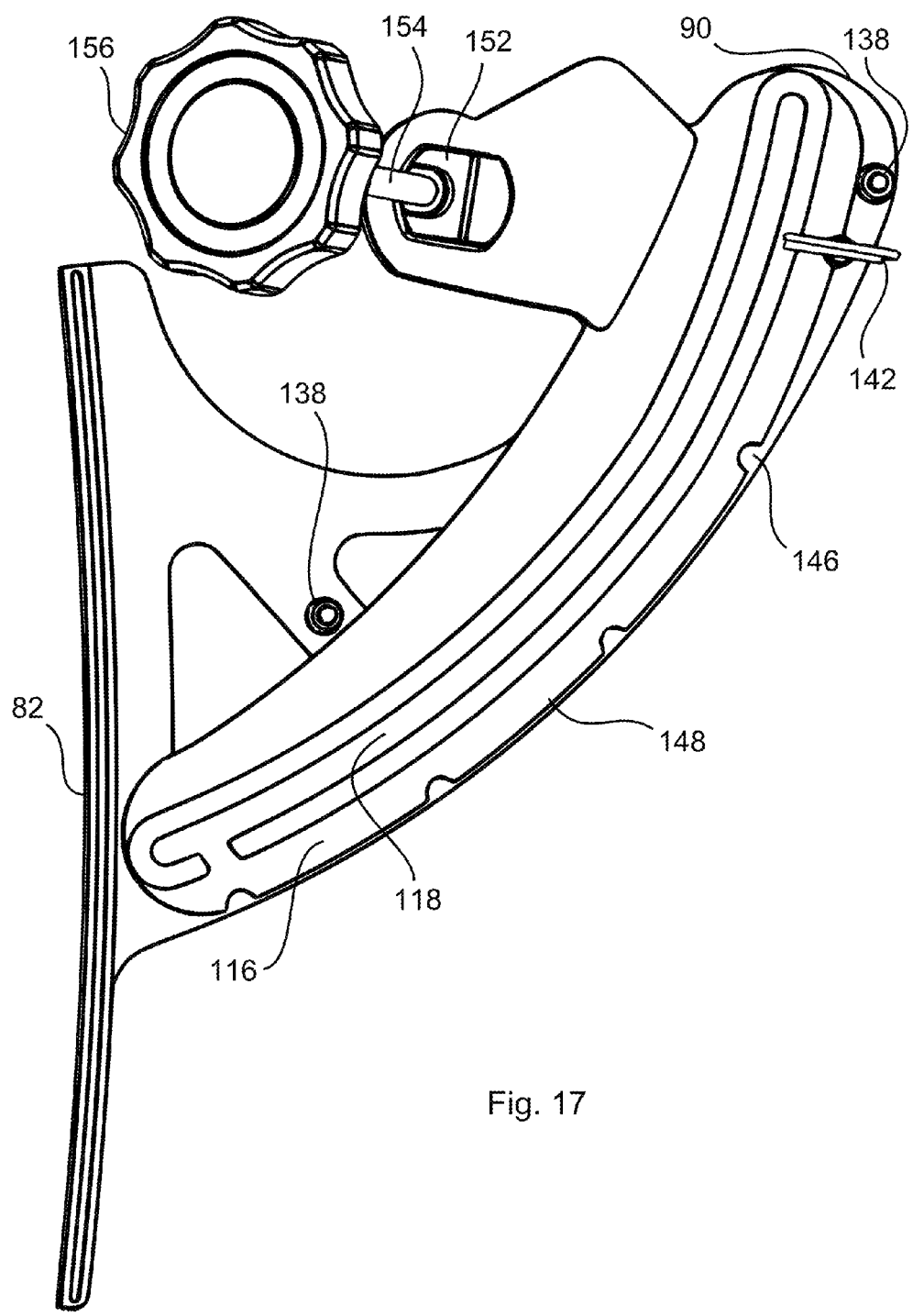
FIG. 17 depicts the connectivity of the first and third arm members of the orthosis of FIG. 9 in a middle flexed position.

Referring to FIGS. 16 and 17, the third arm member 88 can be slidingly affixed to the first arm member 82. The third extension member 116 is slidingly positioned in the first extension member 90, where guide arms 138 of the first extension member 90 support the third extension member 116 in the first extension member 90. Guide pins 140 can be positioned in the channels 118 of the third extension member 116, engaging on opposite sides of the first extension member 90. The guide pins 140 can be used to secure the third extension member 116 in the passage of the first extension member and control the tracking of the third extension member 116 within the first extension member 90, thereby allowing the third extension member 116 to slide along the arcuate path defined by the channels 118, rotating the third arm member 88 with respect to the first arm member 82.

A push pin 142 can be positioned through a push pin hole 144 in the first extension member 90, such that the push pin 142 engages a positioning notch 146 on a bottom edge 148 of the third extension member 116. The push pin 142 prevents relative movement of the third arm member 88 with respect to the first arm member 82.

Figure 18:
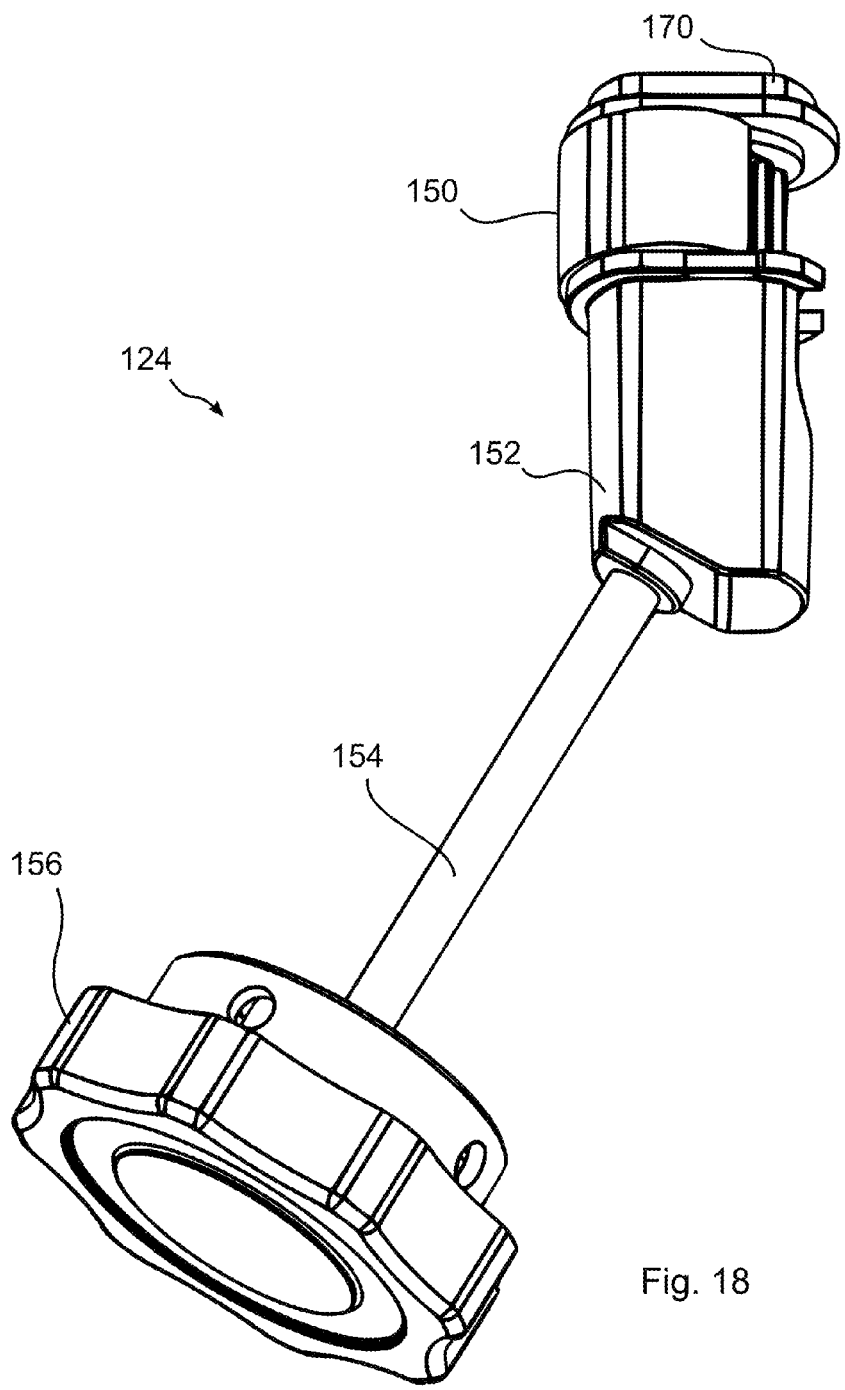
FIG. 18 depicts the drive assembly for the orthosis of FIG. 9.

Referring to FIGS. 15 and 18, the drive assembly 124 is positioned in the drive housing 120 of the third arm member 88. The drive assembly 124 includes a spacer 150 and a gear box 152 covering the gear assembly. A drive shaft 154 is angularly positioned through the gear box 152 to engage the gear assembly 158 (see FIG. 19), where a knob 156 is affixed to the drive shaft 154 for actuation of the gear assembly 158. Drive shaft 154 can be any length such that the patient can comfortably operate knob 156 while the orthosis is in use.

Figure 19:
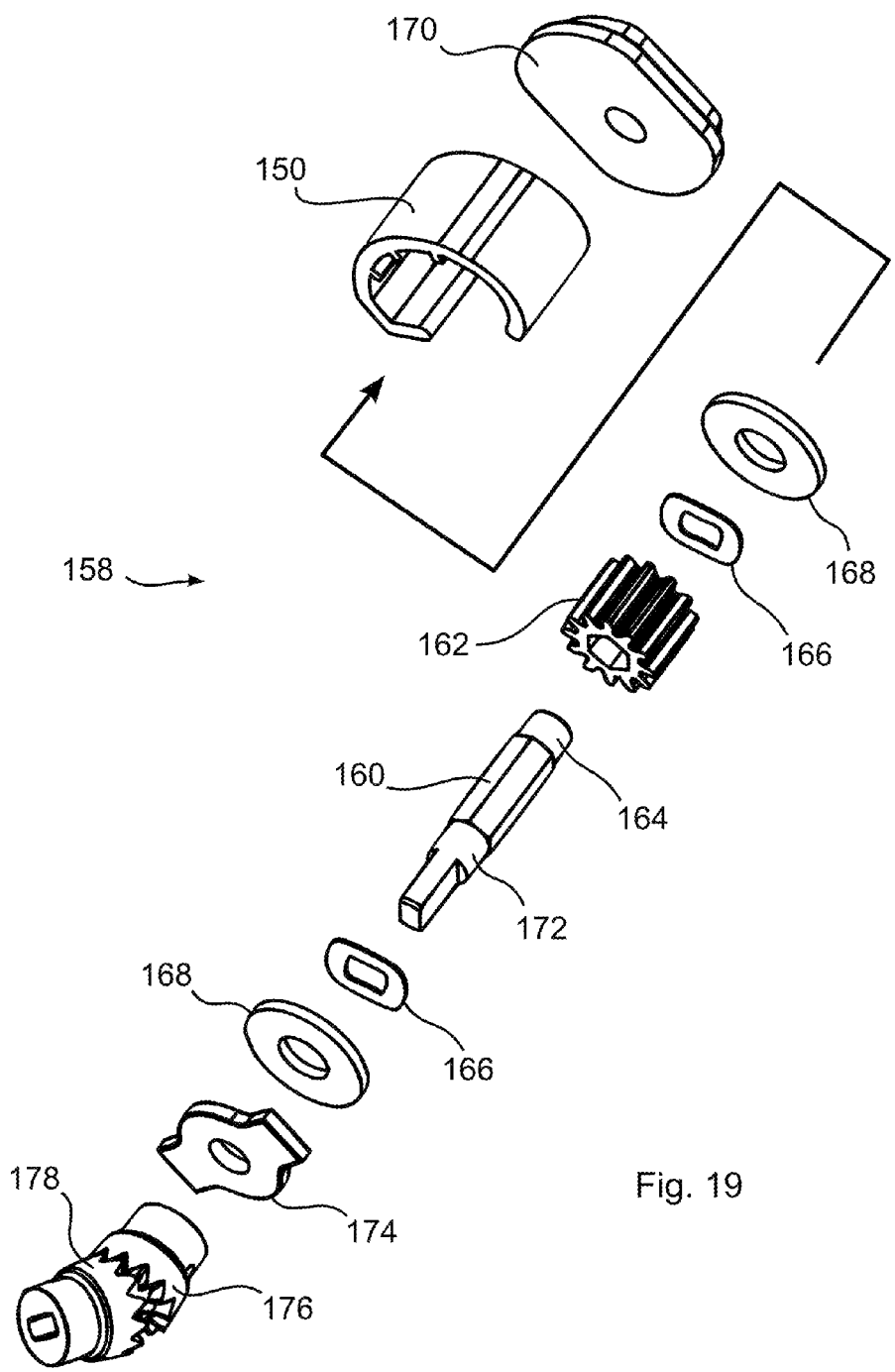
FIG. 19 depicts a gear assembly for the orthosis of FIG. 9.

Referring to FIG. 19, the gear assembly 158 includes a gear shaft 160 having a main gear 162 positioned thereon, such that the main gear 162 rotates with the gear shaft 160. A first end 164 of the gear shaft 160 includes a compression washer 166 and a flat washer 168 mounted thereon, where the first end 164 is rotatably positioned in back cover 170. The compression washer 166 and the flat washer 168 are positioned on the first end 164, such that they are interposed between an end of the main gear 162 and the back cover 170.

A second end 172 of the gear shaft 160 includes a compression washer 166 and a flat washer 168 mounted thereon. A shaft support 174 is positioned on the second end of the gear shaft 160, such that the shaft support 174 and the back cover 170 support the gear shaft 160 in the drive housing 120. The compression washer 166 and the flat washer 168 are positioned on the second end 172 of the gear shaft 160, such that they are interposed between an opposite end of the main gear 162 and the shaft support 174.

A first bevel gear 176 is positioned on the second end 172 of the gear shaft 160, such that a rotation of the first bevel gear 176 rotates the gear shaft 160 and the main gear 162. A second bevel gear 178 angularly engages the first bevel gear 176, such that a rotation of the second bevel gear 178 rotates the first bevel gear 176. The first and second bevel gears 176 and 178 are supported in the gear box 152, where the drive shaft 154 is positioned through the gear box 152, such that an end of the drive shaft 154 engages the second bevel gear 178.

The compression washers 166 are compressed between the ends of the main gear 162, the back cover 170 and the shaft support 174, where the compression washers 166 provide a frictional resistance to the rotation of the main gear 162. In this manner the compression washers 166 prevent a rotation of the main gear 162 without the use of the knob 158 and drive shaft 154 to rotate the gear shaft 160, providing an anti-rotation mechanism.

Figure 20:
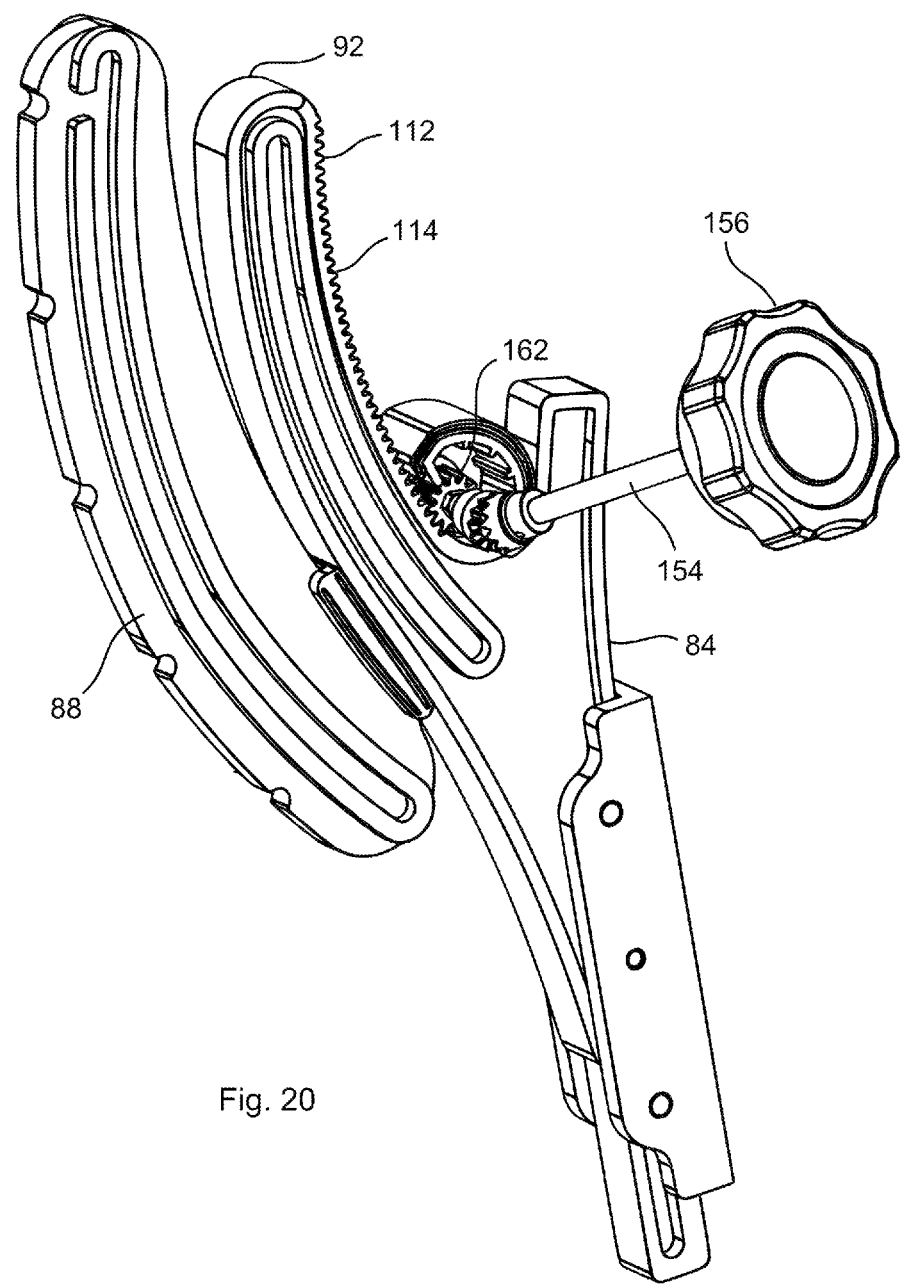
FIG. 20 depicts the connectivity of the drive assembly to the second arm member.

Referring to FIGS. 15 and 20, the second extension member 84 is positioned in the guide channel 122, such that the main gear 162 engages the teeth 114 on the inner surface 112 of the second extension member 84. A rotation of the drive shaft 154 rotates the main gear 162, driving the second extension member 84 through the guide channel 122. A cover plate 134 is positioned over the guide channel 122, securing the second extension member 62 in the guide channel 122 and defining a passage through which it travels.

Guide pins 135 can be positioned in the channels 115 of the second extension member 92, engaging on one side the third arm member 88 and on an opposite side the cover plate 134. The guide pins 135 can be used to secure the second extension member 92 in the passage and control the tracking of the second extension member 92 through the guide channel 122 of the third arm member 88.

Figure 21:
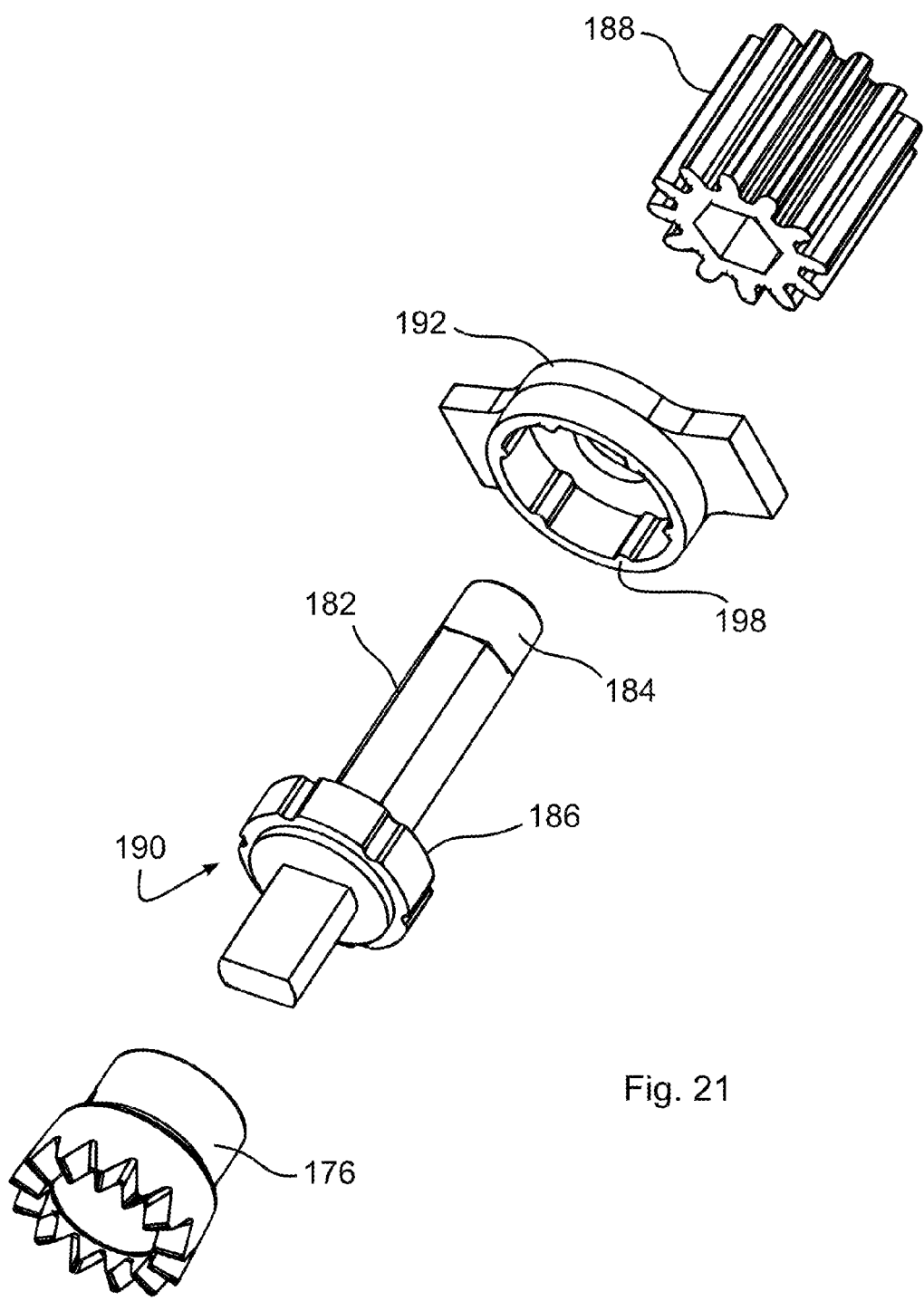
FIG. 21 depicts another drive assembly of the orthosis of FIG. 9.

Referring to FIG. 21, an alternative gear assembly 180 includes a gear shaft 182 having a first end 184 and a second end 186. A main gear 188 is positioned on the gear shaft 182, where the first end 184 of the gear shaft 182 is rotatably positioned in a back cover 170. A second end 186 includes a locking mechanism 190, where the locking mechanism 190 is positioned in a shaft support 192. The locking mechanism 190 engages the first bevel gear 176, and is configured to prevent a rotation of the main gear 188 without the use of the knob 158 and drive shaft 154 to rotate the gear shaft 182, thus providing an anti-rotation mechanism.

Figure 22:
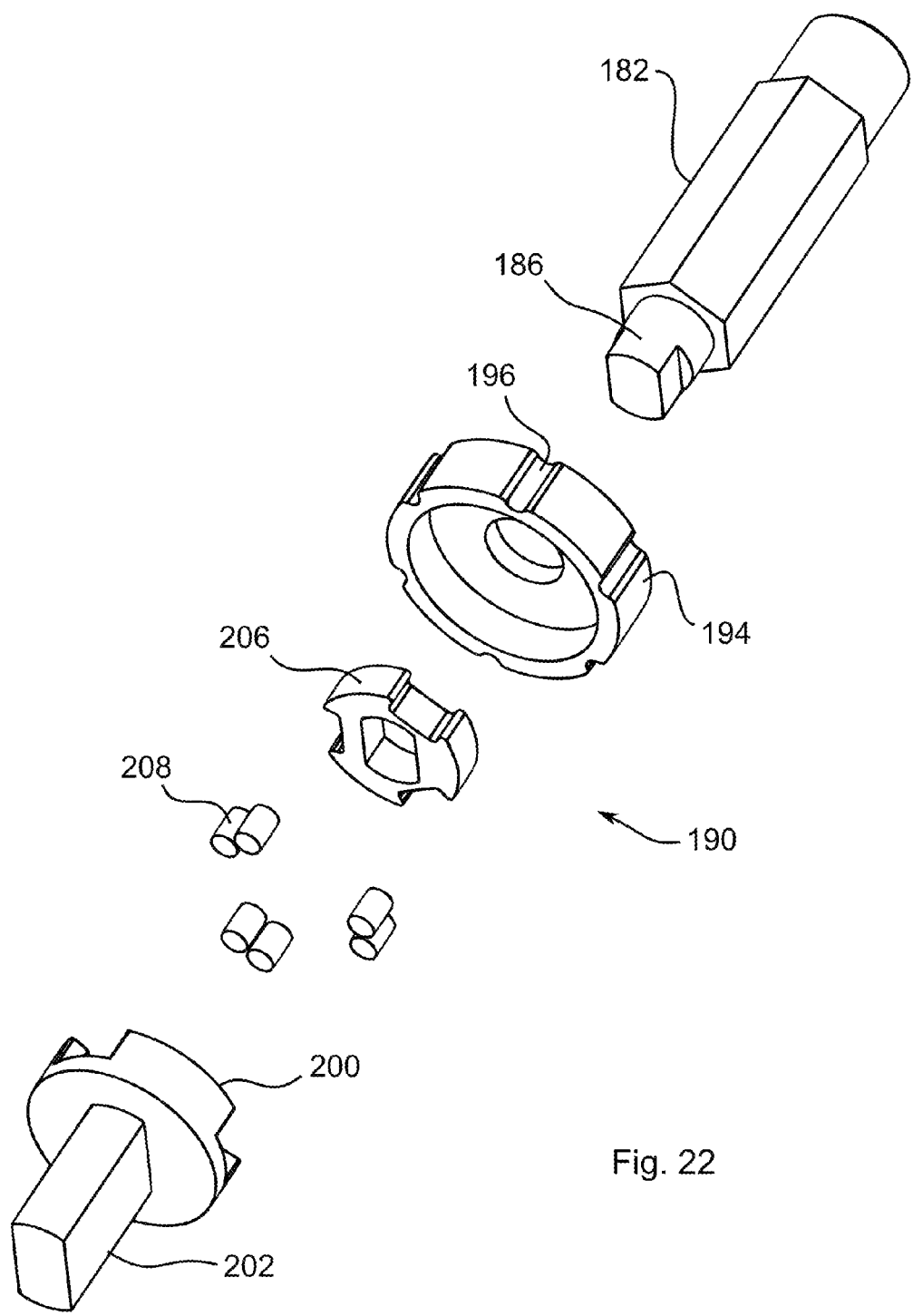
FIG. 22 depicts an exploded view of a locking mechanism for the drive assembly of FIG. 21.
Figure 23:
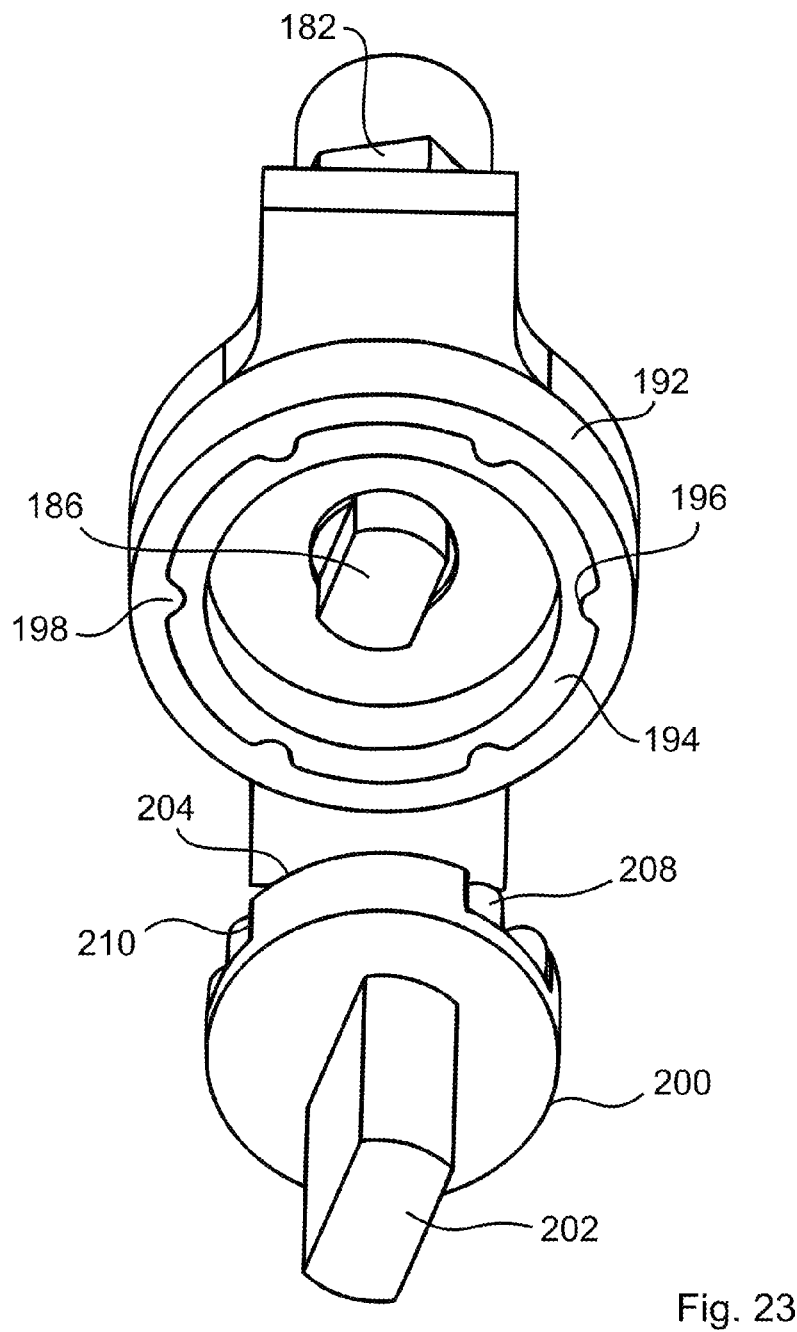
FIG. 23 depicts another exploded front view of a locking mechanism for the drive assembly of FIG. 21.

Referring to FIGS. 22 and 23, the locking mechanism 190 includes an outer sleeve 194 rotatably positioned on the second end 186 of the gear shaft 192. The outer sleeve 194 includes a plurality of notches 196 positioned about an outer surface thereof. The notches 196 are configured to engage a plurality of ridges 198 positioned about an inner surface of the shaft support 192 when the outer sleeve 194 is positioned in the shaft support 192, such that the outer sleeve 194 is locked into positioned within the shaft support 192.

Figure 24:
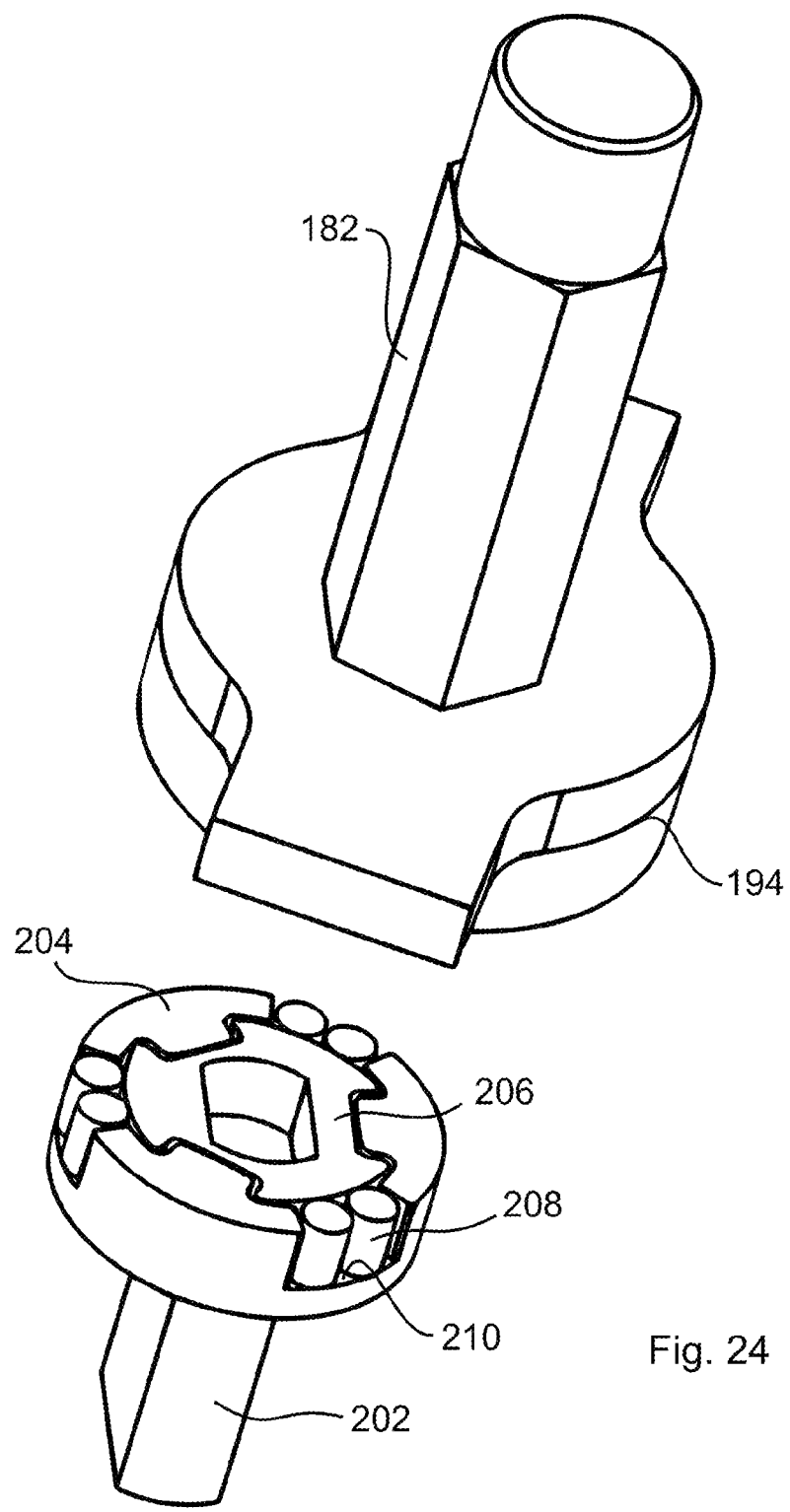
FIG. 24 depicts another exploded rear view of a locking mechanism for the drive assembly of FIG. 21.
Figure 25:
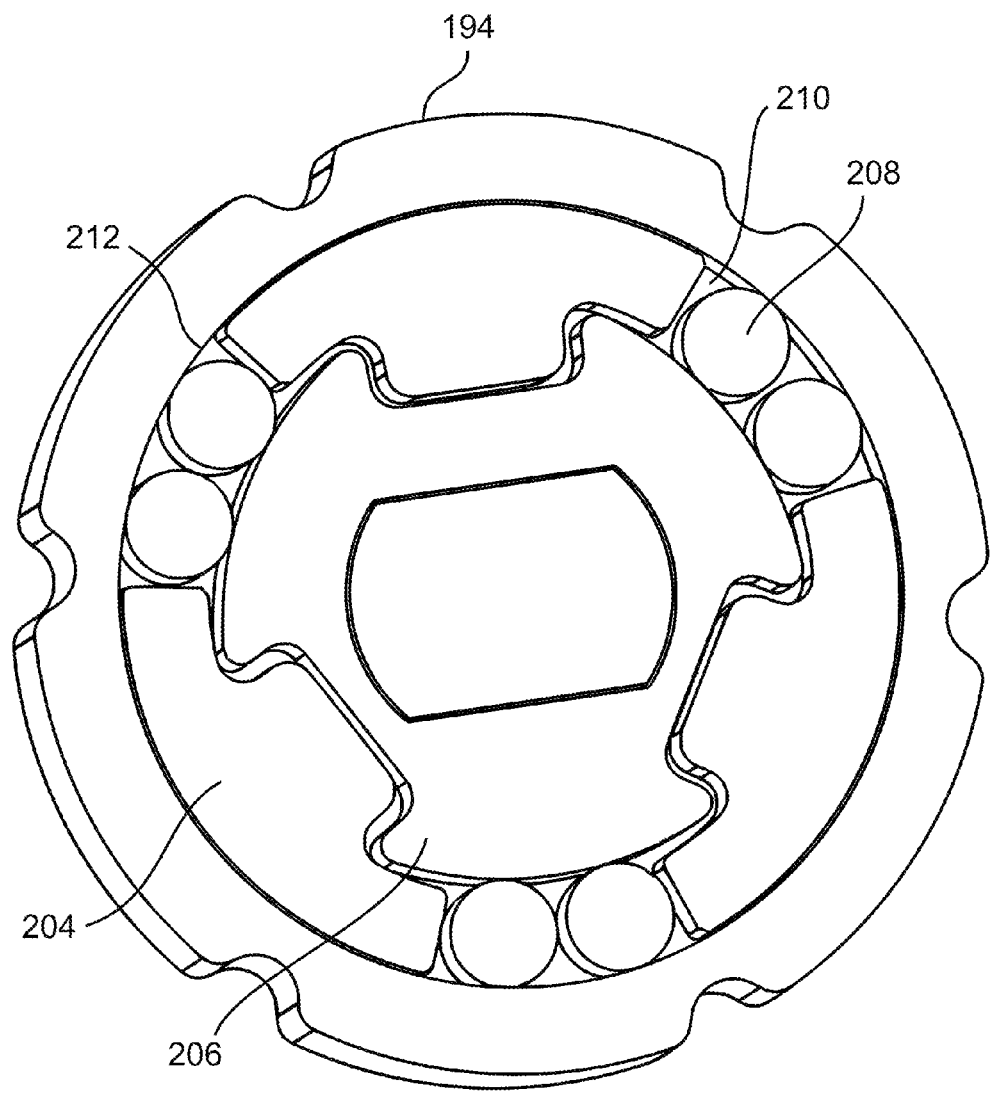
FIG. 25 depicts another sectional front view of a locking mechanism for the drive assembly of FIG. 21.

Referring also to FIGS. 24 and 25, the locking mechanism 190 further includes a drive mechanism 200 having a first end 202 configured to engage the first bevel gear 176 and a second end 204 configured to engage the outer sleeve 194. A bearing plate 206 is positioned in the second end 204 of the drive mechanism 200, where the bearings 208 are positioned within open sections 210 of the second end 204. The bearing 208 are positioned such that the bearing plate 206 supports the bearing 208 within the open sections 210, where a radial section of the circumference of the bearings 208 protrudes past an outer surface of the second end 204.

The second end 204 of the drive mechanism 200 is press fitted into the outer sleeve 194, such that bearing plate 206 engages the second end 186 of the gear shaft 182 and the bearings 208 are compressed between the bearing plate 206 and the inner surface 212 of the outer sleeve 194. The compressive force between the bearing plate 206, the bearings 208, and the inner surface 212 of the outer sleeve 194 is sufficient to prevent a rotation of the main gear 188 without the use of the knob 158 and drive shaft 154 to rotate the gear shaft 182, thus providing an anti-rotation mechanism.

Figure 26:
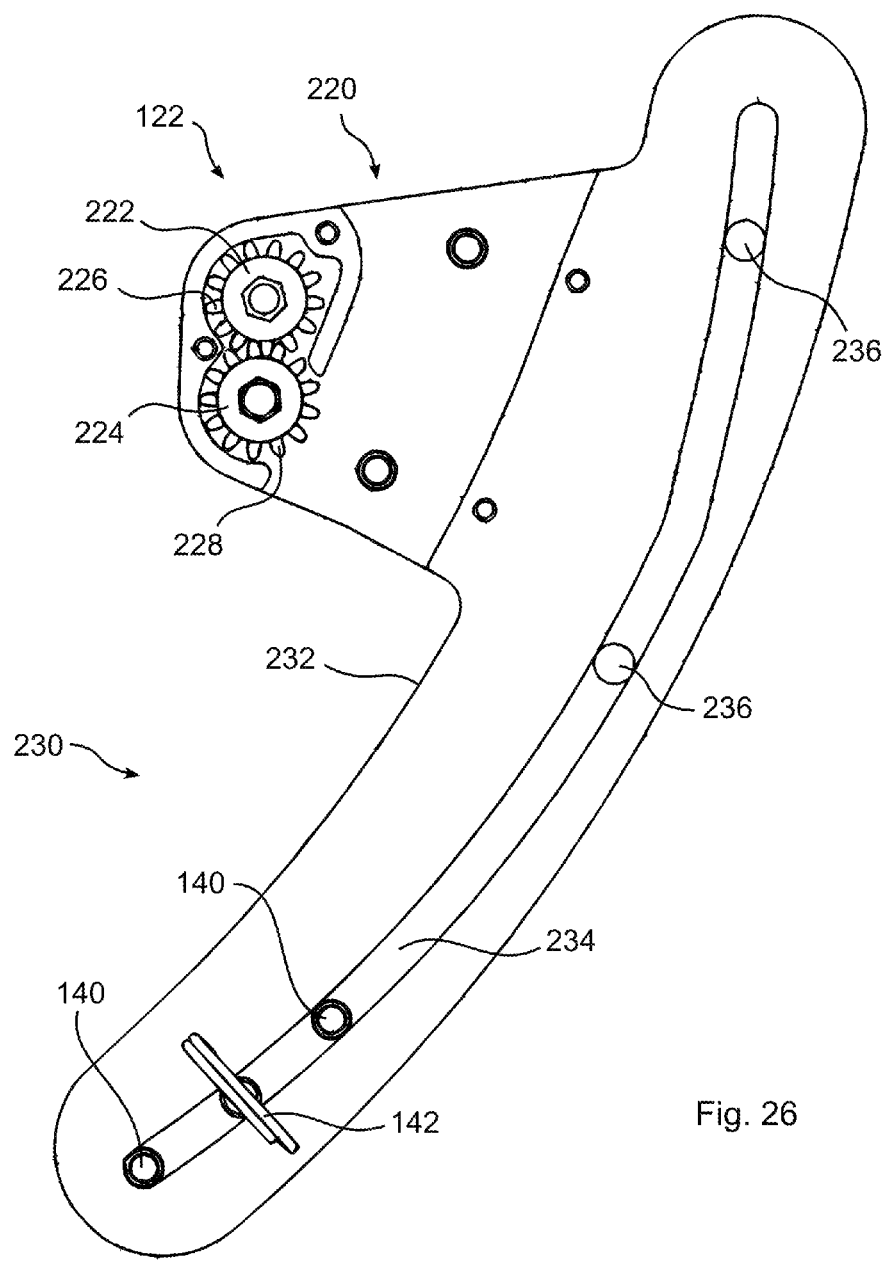
FIG. 26 depicts an alternative third arm member for the orthosis of FIG. 9.

Referring to FIGS. 15 and 26 another drive assembly 220 includes a drive gear 222 and a main gear 224, where the teeth 226 of the drive gear 222 engage the teeth 226 of the main gear 224. The drive shaft 154 is connected to the drive gear 222, extending through the cover plate 134. A rotation of the drive shaft 154 rotates the drive gear 222, which in turn rotates the main gear 224. The main gear 224 is sized such that a portion of the gear teeth 228 protrudes into the guide channel 122 of the third arm member 88, thereby engaging the gear teeth 114 of the second arm member 84.

Referring also to FIG. 26, an alternative third arm member 230 includes a third extension member 232 having an arcuate shape, where the radius of curvature of the third extension member 232 is a function of the joint to be treated and the degree of extension contractures. The third extension member 232 includes channels 234 disposed on opposite sides thereof. A drive housing 120 is positioned proximal to a guide channel 122, where the drive housing 120 includes a drive assembly 124.

The third arm member 230 can be slidingly affixed to the first arm member 82, where the third extension member 232 is slidingly positioned in the first extension member 90, where guide arms 138 of the first extension member 90 supports the third extension member 232 in the first extension member 90. Guide pins 140 can be positioned in the channels 234 of the third extension member 232, engaging on opposite sides of the first extension member 90. The guide pins 140 can be used to secure the third extension member 232 in the passage of the first extension member and control the tracking of the third extension member 232 within the first extension member 90, thereby allowing the third extension member 232 to slide along the arcuate path defined by the channels 234, rotating the third arm member 88 with respect to the first arm member 82.

A push pin 142 can be positioned through a push pin hole 144 in the first extension member 90, such that the push pin 142 is positioned through a push pin hole 236 in the channels 234 of the third extension member 232. The push pin 142 prevents relative movement of the third arm member 230 with respect to the first arm member 82.

In an exemplary use, the orthosis 80 is operated to extend a knee joint in the following manner. The first cuff 94 is fastened about the upper leg portion tightly enough that the first arm member 82 may apply torque to the upper leg portion without having the first cuff 94 slide along the upper leg portion. Similarly, the second cuff 96 is fastened securely around the lower leg portion so that the second arm member 84 may apply torque to the lower leg portion without the second cuff 96 sliding along the lower leg portion. The orthosis 80 is attached to the upper and lower leg portions in a first position. The second arm member 84 is rotated from the first position to a second position, relative to the first arm member 82, rotating the lower leg portion about the joint axis 86 stretching the joint. The orthosis 80 is maintained in the second position for a predetermined treatment time providing a constant stretch to the joint. Additionally, the second extension member 92 can be made of a substantially rigid but flexible material, such that while the second arm member 84 is in the second position the second extension member 92 acts like a spring, providing dynamic stretch to the connective tissue of the joint.

After the expiration of the treatment time, the second arm member 84 is moved back to the first position, relieving the joint. Optionally, the second arm member 84 can be rotated to a third position, increasing the stretch on the joint. The second arm member 84 can be rotated at discrete time intervals to incrementally increase the stretch of the joint through the treatment cycle. After completion of the treatment cycle, the second arm member 84 is returned to the first position for removal of the orthosis 80.

In another exemplary use, the push pin 144 is removed from the first and third arm members 82 and 88, such that the third arm members 88 is moved from a first position to a second position with respect to the first arm member 82, the third arm member 88 can slide along the arcuate path of the third extension 116 of the third arm member 88. The third arm member 88 can be adjusted with respect to the first arm member 82 in 0 degree to 22 degree increments. In an embodiment, the third arm member 88 can be adjusted with respect to the first arm member 82 in 11 degree increments.

The gear teeth 114 of the second arm member can have a travel range of approximately 29 degrees. The adjustment of the third arm member 88 with respect to the first arm member 82 can be utilized to increase the range on motion of the orthosis 80. It is thus contemplated that the orthosis 80 can have a range of motion from around 45 degrees flexion to about 15 degrees hyper-extension.

Although orthosis 80 has been primarily described as useful for extension, orthosis 80 can also be used for increasing range of motion in flexion. For example, orthosis 80 can be placed on the anterior aspect of the upper and lower leg to increase range of motion in extension. Placing orthosis 80 on the posterior aspect of the upper and lower leg would increase range of motion in flexion.

In this regard, FIGS. 27-32 show an embodiment of an orthosis 280 particularly useful for increasing range of motion of a knee joint in flexion. The knee orthosis 280 of this embodiment is similar to the embodiments described above, and also includes a first arm member 242 having a first extension member 244, a second arm member 246 having a second extension member 248, and third arm member 250 interposed between the first and second arm members 242 and 246.

The third arm member 250 is slidingly positioned in the first extension member 244, and a push pin 252 can be positioned through a push pin hole 254 in the first extension member 244 so that the push pin 252 prevents relative movement of the third arm member 250 with respect to the first arm member 242. Moving the push pin 252 to a different push pin hole 254 allows the user to change the arc to closely match the user's maximum range of motion. In a preferred embodiment, the push pin holes 254 are located on the first extension member 244 in locations allowing for approximately 30 degrees of movement before needing to relocate the push pin 252. The push pin holes 254 are preferably located in positions allowing a range from 58 degrees flexion to 148 degrees flexion.

Figure 27:
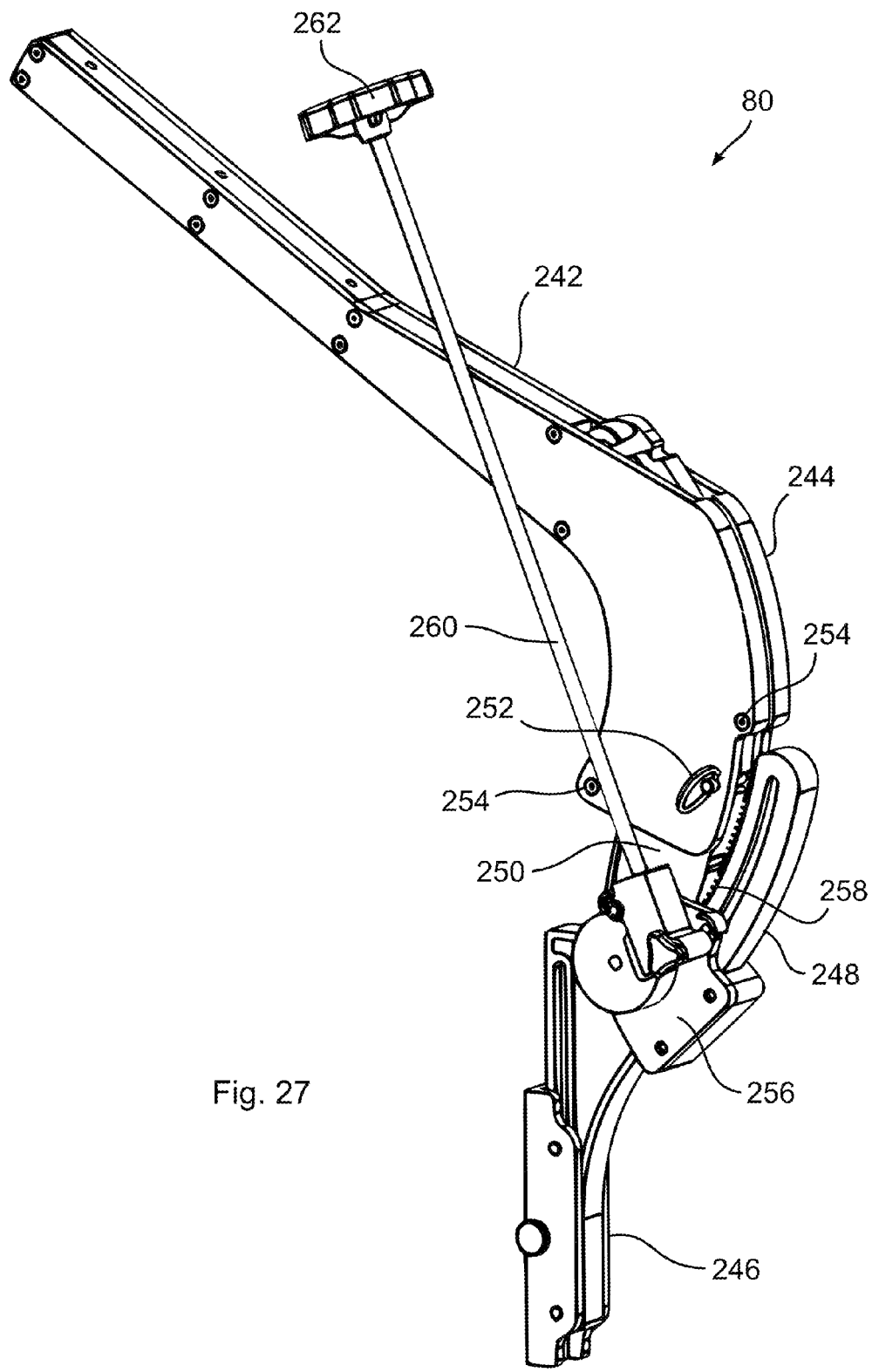
FIG. 27 depicts a knee flexion orthosis of the present invention in an engaged position.
Figure 28:
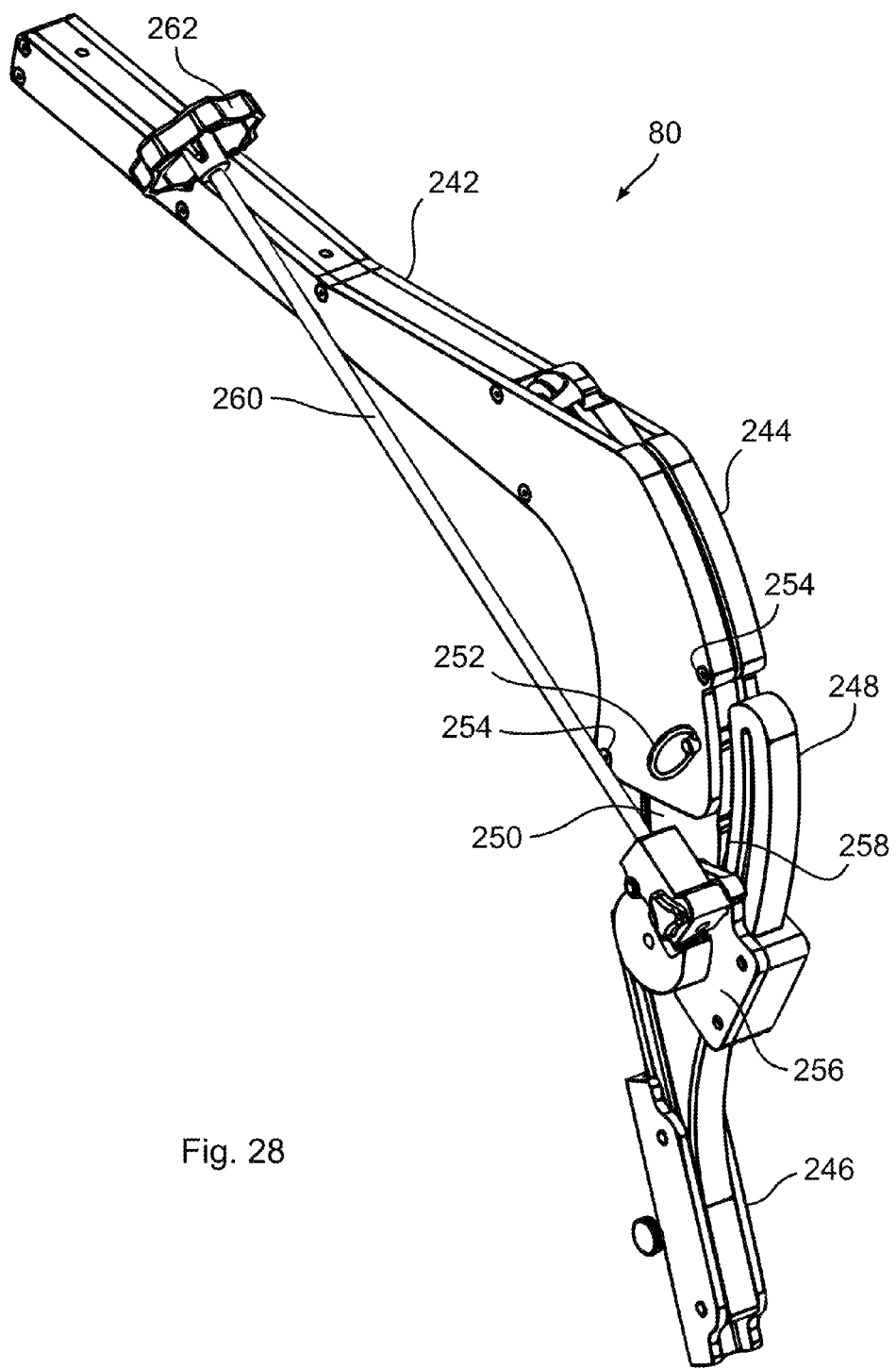
FIG. 28 depicts the knee flexion orthosis of the present invention in a disengaged position.

Referring also to FIGS. 27 and 28, the second extension member 248 is positioned in the guide channel of the drive assembly 256, such that the drive assembly 256 engages the teeth 258 on the inner surface of the second extension member 248. An actuation of the drive assembly 256 drives the second extension member 248 through the guide channel, defining a passage through which the second extension member 248 travels during flexion of the knee joint by the user. In a preferred embodiment, the drive assembly 256 is capable of disengaging from the teeth 258 by moving the drive shaft 260. FIG. 27 shows the drive assembly 256 of the orthosis 280 in the engaged position, and FIG. 28 shows the drive assembly 256 after it has been lowered and in a disengaged position. The ability to disengage the drive assembly 256 allows for the drive assembly 256 to move freely for quicker adjustments. Furthermore, the drive shaft 260 extends up to the user so that the knob 262 is easily within reach of the user to disengage the drive assembly 256 and/or rotate the drive shaft 260.

Figure 29:
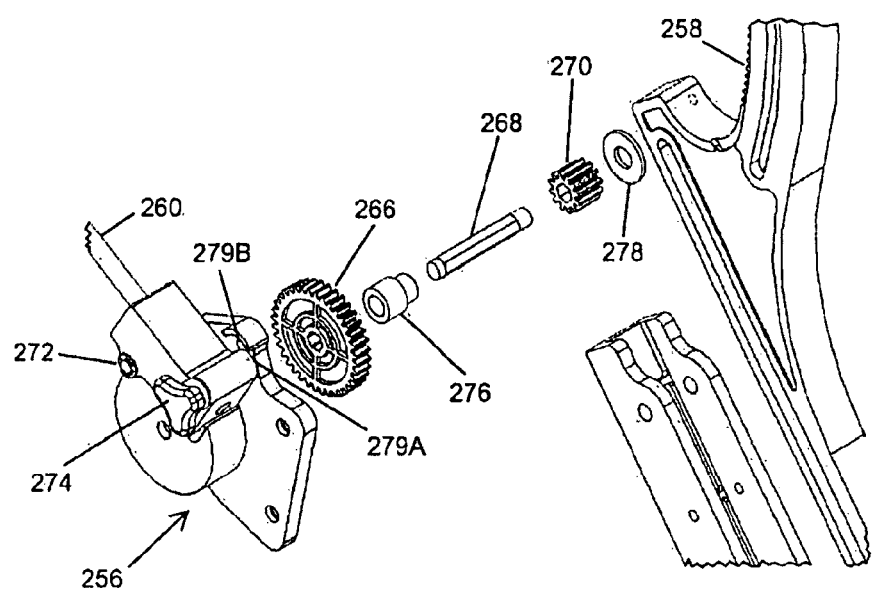
FIG. 29 shows an exploded view of a drive assembly for the orthosis of FIGS. 27 and 28.
Figure 30:
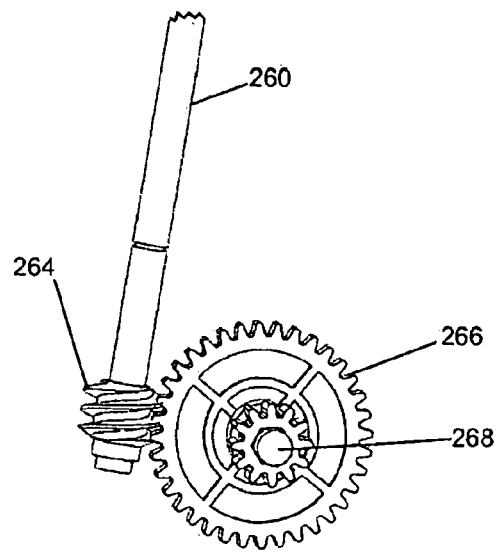
FIG. 30 depicts the engagement of the worm gear with the driven gear of FIG. 29.

FIGS. 29 and 30 show one embodiment in which drive assembly 256 can be selectively engageable and disengageable. Drive shaft 260 is movable between an engaged position (shown in FIGS. 27 and 29) and a disengaged position (shown in FIG. 28). In the engaged position, a worm gear 264 on the distal end of drive shaft 260 engages driven gear 266 such that rotation of drive shaft 260 results in rotation of worm gear 264 and initiates rotation of driven gear 266. The rotation of driven gear 266 causes rotation of gear shaft 268 and main gear 270, which is in engagement with teeth 258. A spacer 276 keeps gears 266, 270 in the desired location and a washer 278 is also located on shaft 268.

As is well known, the teeth in worm gear 264 can be configured to prevent back-off. Alternatively and as discussed above, one or more washers can be positioned to provide resistance to rotation and prevent back-off. Thus, in the engaged position, main gear 270 does not move unless knob 262 is rotated. In contrast, when drive shaft 260 is in the disengaged position, main gear 270 can freely rotate and travel against teeth 258. As shown, drive shaft 260 is pivotable about pivot point 272 between the engaged and disengaged positions. Release pin 274 can be placed in either a first hole 279*a* (engaged position) or a second hole 279*b* (disengaged position).

Figure 31:
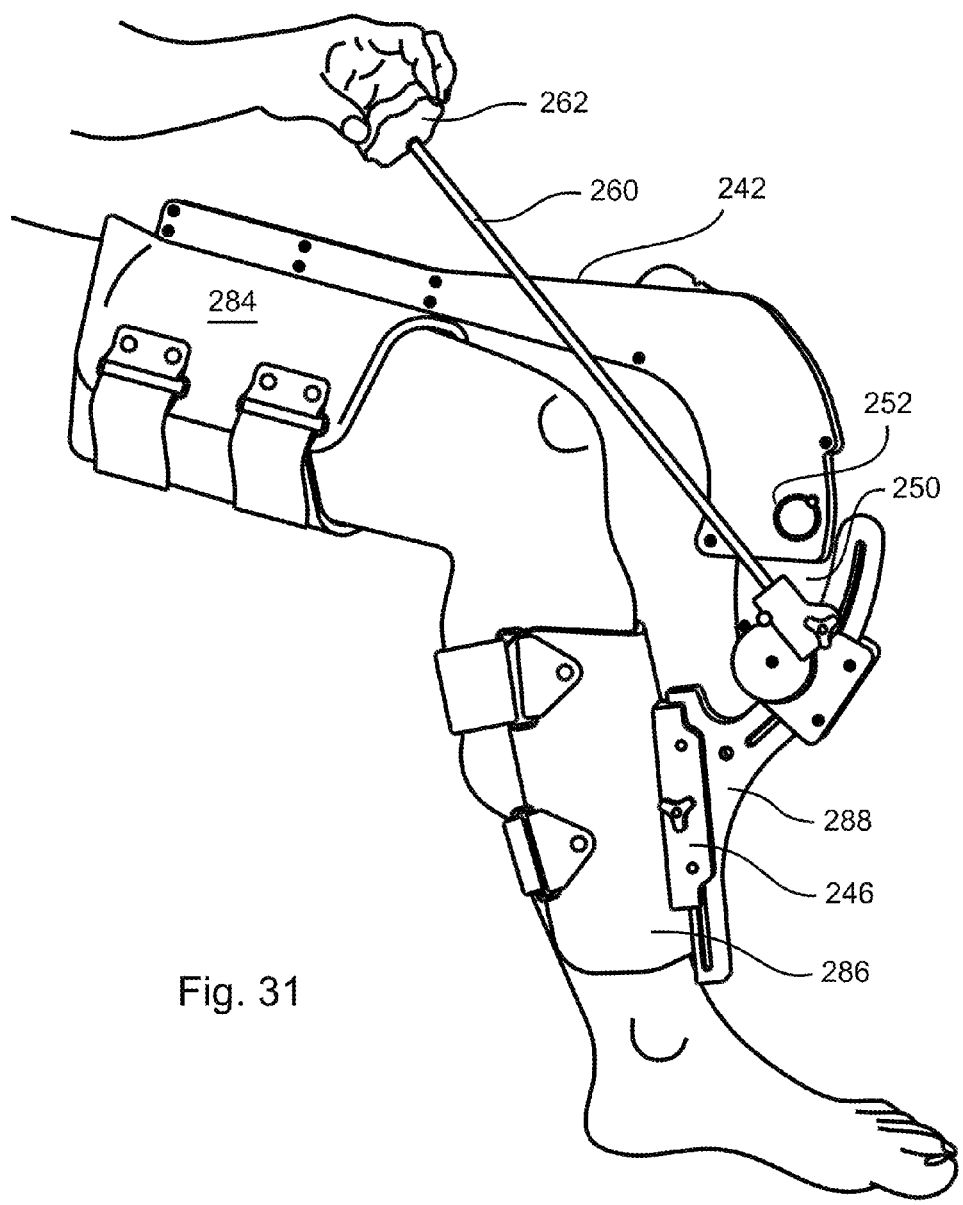
FIG. 31 shows the orthosis of FIGS. 27 and 28 on a patient.
Figure 32:
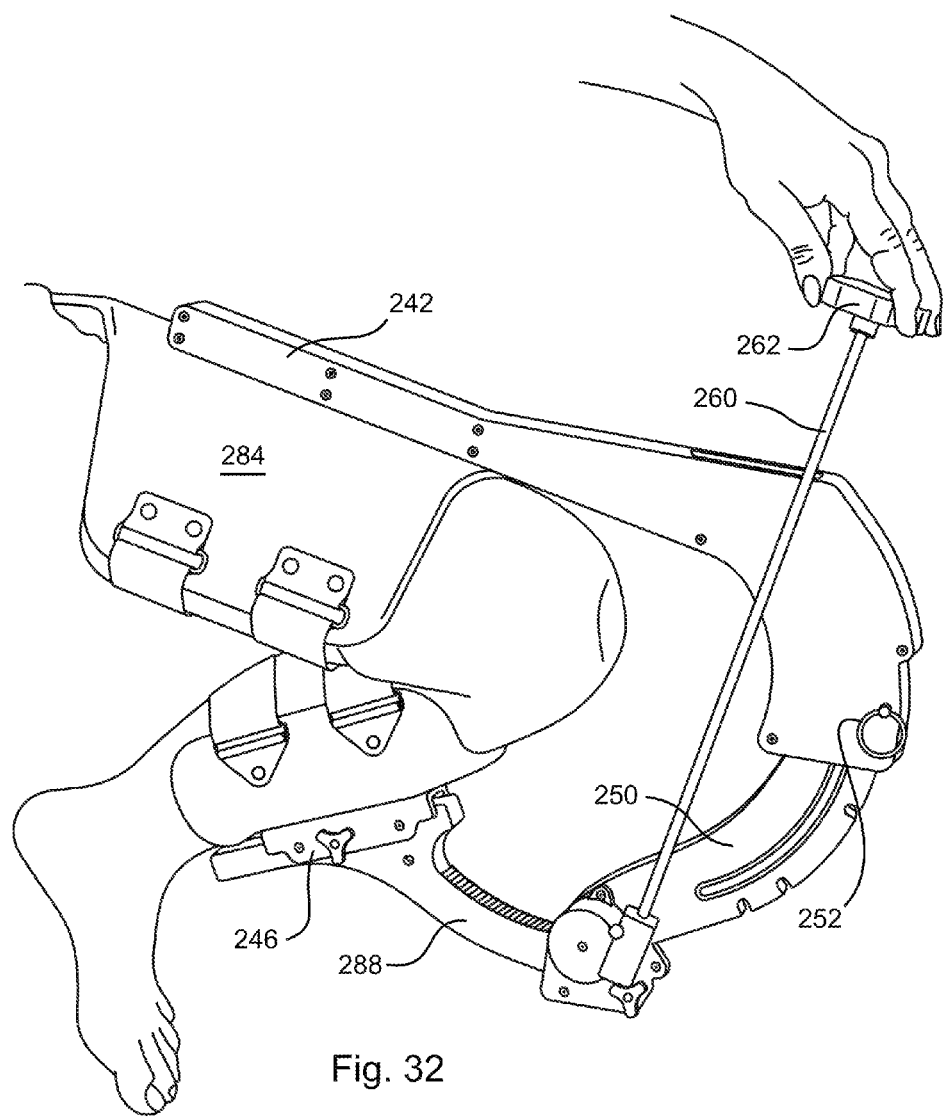
FIG. 32 shows the orthosis of FIG. 31 in full flexion.

In an exemplary use shown in FIGS. 31 and 32, the orthosis 280 is operated to flex a knee joint in the following manner. A first cuff 284 is fastened about the upper leg portion tightly enough that the first arm member 242 may apply torque to the upper leg portion without having the first cuff 284 slide along the upper leg portion. Similarly, the second cuff 286 is fastened securely around the lower leg portion so that the second arm member 246 may apply torque to the lower leg portion without the second cuff 286 sliding along the lower leg portion. The orthosis 280 is attached to the upper and lower leg portions in a first position (FIG. 31). The second arm member 246 is rotated from the first position to a second position, relative to the first arm member 242, rotating the lower leg portion about the joint axis stretching the joint. The orthosis 280 is maintained in the second position for a predetermined treatment time providing a constant stretch to the joint. Additionally, the second extension member 248 can be made of a substantially rigid but flexible material, such that while the second arm member 246 is in the second position the second extension member 248 acts like a spring, providing dynamic stretch to the connective tissue of the joint.

After the expiration of the treatment time, the second arm member 246 is moved back to the first position, relieving the joint. Optionally, the second arm member 246 can be rotated to a third position, increasing the stretch on the joint. The second arm member 246 can be rotated at discrete time intervals to incrementally increase the stretch of the joint through the treatment cycle. After completion of the treatment cycle, the second arm member 246 is returned to the first position for removal of the orthosis 280.

In another exemplary use, the push pin 252 is removed from the first and third arm members 242 and 250, such that the third arm members 250 is moved from a first position to a second position with respect to the first arm member 242, the third arm member 250 can slide along the arcuate path of the third extension 288 of the third arm member 250. As a result and analogous to orthosis 80, the third arm member 250 can be adjusted with respect to the first arm member 242. In an embodiment, the third arm member 250 can be adjusted with respect to the first arm member 242 in approximately 20 degree increments.

The gear teeth 258 of the second arm member can have a travel range of approximately 90 degrees. The adjustment of the third arm member 250 with respect to the first arm member 242 can be utilized to increase the range on motion of the orthosis 280. It is thus contemplated that the orthosis 280 can have a range of motion from around 58 degrees flexion to about 158 degrees flexion.

Although orthosis 280 has been primarily described as useful for flexion, orthosis 280 can also be used for increasing range of motion in flexion. For example, orthosis 280 can be placed on the anterior aspect of the upper and lower leg to increase range of motion in flexion. Placing orthosis 280 on the posterior aspect of the upper and lower leg would increase range of motion in extension.

For either orthosis 80 or orthosis 280, the first, second, and third arm members are rigid members made of, for example, aluminum, stainless steel, polymeric, or composite materials. The arms are rigid so as to be able to transmit the necessary forces. It should be understood that any material of sufficient rigidity can be used.

In an embodiment, the components of the orthosis 80, 280 of the present invention are made by injection molding. Generally for injection molding, tool and die metal molds of the orthosis 80, 280 components are prepared. Hot, melted plastic material is injected into the molds. The plastic is allowed to cool, forming components. The components are removed from the molds and assembled. The cuff portions can be individual molded and attached to the arm members. Alternatively, the cuff portions can be molded as an integrated part of the arm members.

Similarly, the gears are rigid members made of, for example, aluminum, stainless steel, polymeric, or composite materials. The gears are rigid so as to be able to transmit the necessary forces.

In the above description, the second and/or third extension members are shown and described as having a substantially circular arcuate shape, positioning the axis of rotation at the joint axis. However, it is contemplated that the second and/or third extension members and can have alternative shapes.

The drive assemblies are described as utilizing a gear system. However, it is contemplated that other known drive systems can be used to move the first extension member with respect to the second extension member, for example a friction type drive system. Regardless of the drive system used, the joint orthosis of the present invention can act as a brace, restricting the relative movement of the first and second body portions to one degree of freedom (e.g. flexion and extension about the joint). Thus, drive assemblies can be configured to allow free motion in one degree of freedom. This can be achieved in a number of different ways. For example, the gears can be positioned such that it does not engage teeth.

In an alternative embodiment, the drive assembly of orthosis 80, 280 in accordance with the present invention can be actuated by a motor instead of by a manually actuatable member, such as the knob 156, 262. Likewise, the motor may be configured and adapted with gearing that causes the orthosis to cycle through a range of motion in a predetermined manner, or alternatively maybe controlled by a programmable logic controller (PLC).

In an embodiment, an electric motor is mounted to the shaft 154, 268 for rotation of the gears. A battery provides electric power to the motor. Alternatively, the motor can be supplied with external power. A microprocessor controls the operation of the motor. The microprocessor and motor together can be used to cycle the second and third arm members through extension and flexion; to move the first and second arm members in one pivotal direction a certain amount, hold there while tissue stretches, then move further in that direction; or in any other manner.

In another manner of use, the orthosis can be set to cycle to one end of the joint's range of motion and hold there for a predetermined period of time, then cycle to the other end of the joint's range of motion and hold there. The programming and control of the microprocessor is within the skill of the art as it relates to driving the motor to control the second and third arm members 84 and 88 to move in known manners. This embodiment is ideally suited for continuous passive motion exercise, because the orthosis is portable and because the motor can be programmed with the desired sequence of movements.

It should be understood that the particular physical arrangement of the motor, the battery, and the microprocessor is not the only possible arrangement of those elements. The invention contemplates that other arrangements of these or similarly functional elements are quite suitable, and thus, the invention is intended to cover any such arrangement. Additionally, another type of power source, other than an electric motor, can also be used. For example, the use of a hydraulic or pneumatic motor as the drive mechanism is contemplated.

The present invention can further include a monitor for use with the orthosis 80, 280, which provides assurances the patient is properly using the orthosis 80, 280 during his/her exercise period. For instance, the monitor can have a position sensor, a temperature sensor, a force sensor, a clock or timer, or a device type sensor for monitoring the patient's implementation of a protocol. The information obtained from these monitoring devices may be stored for later analysis or confirmation of proper use or may be transmitted in real-time during use of the device. The data obtained from the monitor can be analyzed by a healthcare professional or technician and the protocol can be adjusted accordingly.

This analysis may be conducted remotely, thereby saving the time and expense of a home visit by a healthcare professional or technician. An exemplary monitoring system is provided in U.S. Publication No. 20040215111 entitled "Patient Monitoring Apparatus and Method for Orthosis and Other Devices," to Bonutti et al., the content of which is herein expressly incorporated by reference in its entirety.

The components of the present invention are rigid members made of, for example, aluminum, stainless steel, polymeric, or composite materials. The member and extensions are sufficiently rigid to transmit the necessary forces. It should be understood that any material of sufficient rigidity might be used. For example, some components can be made by injection molding. Generally, for injection molding, tool and die metal molds of the components are prepared. Hot, melted plastic material is injected into the molds. The plastic is allowed to cool, forming components. The components are removed from the molds and assembled.

Furthermore, it is contemplated that the components can be made of polymeric or composite materials such that the device can be disposable. For example, at least some or all of the components can be made of a biodegradable material such as a biodegradable polymer. Among the important properties of these polymers are their tendency to depolymerize relatively easily and their ability to form environmentally benign byproducts when degraded or depolymerized. One such biodegradable material is poly (hydroxyacids) ("PHA's") such as polyactic acid ("PLA") and polyglycolic acid ("PGA").

Additionally, the device can be made of a nonmagnetic material. In such instance, the device can be used as a positioning device for use in imaging devices, such as a MRI device. It is also contemplated that the device can be used as a positioning device for use during surgical procedures, where it may be necessary to adjust and hold the position of the joint.

It will be appreciated by persons skilled in the art that the present invention is not limited to what has been particularly shown and described herein above. For example, although the examples presented identify the wrist joint, the present invention can be used for any joint. In addition, unless mention was made above to the contrary, it should be noted that all of the accompanying drawings are not to scale. A variety of modifications and variations are possible in light of the above teachings without departing from the scope and spirit of the invention.

What is claimed:

1. A knee orthosis for stretching tissue around a knee joint of a patient between upper and lower leg portions, the knee joint and the upper and lower leg portions defining on one side of the knee joint an inner sector which decreases in angle as the knee joint is flexed and defining on the opposite side of the knee joint an outer sector which decreases in angle as the knee joint is extended, comprising:
   a first arm member;
   an upper leg cuff secured to the first arm member and configured to be secured to the upper leg portion;
   a second arm member operatively connected to the first arm member;
   a lower leg cuff secured to the second arm member and configured to be secured to the lower leg portion; and
   a drive assembly operatively connecting the first and second arm members and configured to selectively move the second arm member with respect to the first arm member, wherein the drive assembly includes a drive shaft having opposite first and second ends, a knob at the first end of the drive shaft, a worm at the second end of the drive shaft, and a driven gear in meshing engagement with the worm,
   wherein the drive shaft extends at an offset angle relative to the first arm member, wherein the offset angle is less than 90 degrees.

2. The knee orthosis of claim 1, wherein the drive assembly includes an anti-rotation mechanism.

3. The knee orthosis of claim 1, wherein the drive shaft extends upward relative to the second arm member.

4. The knee orthosis of claim 1, wherein the knob is accessible by a hand of the patient when the knee orthosis is donned on the patient's knee.

5. The knee orthosis of claim 1, wherein the first arm member is connected to an anterior side of the upper leg cuff, wherein the second arm member is connected to an anterior side of the lower leg cuff.

* * * * *